United States Patent [19]
Kendall et al.

[11] Patent Number: 5,861,484
[45] Date of Patent: Jan. 19, 1999

[54] INHIBITOR OF VASCULAR ENDOTHELIAL CELL GROWTH FACTOR

[75] Inventors: Richard L. Kendall, Edison; Kenneth A. Thomas, Jr., Chatham Borough, both of N.J.

[73] Assignee: Merck & Co., Inc., Rahway, N.J.

[21] Appl. No.: 786,164

[22] Filed: Jan. 21, 1997

Related U.S. Application Data

[60] Division of Ser. No. 232,538, Apr. 21, 1994, Pat. No. 5,712,380, and a continuation-in-part of Ser. No. 38,769, Mar. 25, 1993, abandoned.

[51] Int. Cl.$^6$ .......................... C07K 14/00; A61K 38/02
[52] U.S. Cl. ................................................ 530/350; 514/2
[58] Field of Search ............................. 530/350; 514/2; 435/69.1

[56] References Cited

FOREIGN PATENT DOCUMENTS

WO92/14748  9/1992  WIPO.

OTHER PUBLICATIONS

Shibuya et al., Oncogene, 5, 519–524, 1990.
Duan et al., J. Biol. Chem., 266, 413–418, Jan. 1991.
Terman et al., Biochem and Biophysical Res. Commun., 187, 1579–1586, Sep. 1992.
Terman et al., On Cogene, 6, 1677–1683, 1991.
Conn et al., Amino acid and cDNA sequences of a vascular endothelial cell mitogen that is homologous to platelet–derived growth factor, (1990) Proc. Natl. Acad. Sci. U.S.A., 87, pp. 2628–2632.
Ferrara and Henzel, Pituitary Follicular Cells Secrete A Novel Heparin–Binding Growth Factor Specific For Vascular Endothelial Cells, (1989) Biochem. Biophys. Res. Comm., 161, pp. 851–858.
Gozpadorowicz et al., Isolation and characterization of a vascular endothelial cell mitogen produced by pituitary–derived folliculo stellate cells, (1989) Proc. Natl. Acad. Sci. U.S.A., 86 pp. 7311–7315.
Connolly, D.T. et al., Vascular Permeability Factor, an Endothelial Cell Mitogen Related to PDGF, (1989) Science, 246 pp. 1309–1312.
DeVries, C. et al., The fms–Like Tyrosine Kinase, a Receptor for Vascular Endothelial Growth Factor, (1992) Science 255 pp. 989–991.
Terman, B.I. et. al., Identification of a new endothelial cell growth factor receptor tyrosine kinase, (1991) Oncogene 6, pp. 1677–1683.

Terman, B.I. et. al., Identification of the KDR Tyrosine Kinase As A Receptor For Vascular Endothelial Cell Growth Factor, (1992) Biochem. Biophys. Res. Comm., 187, pp. 1579–1586.
Shibuya, M. et. al., Nucleotide Sequence and expression of a novel human receptor–type tyrosine kinase gene (flt) closely related to the fms family, (1990) Oncogene, 5, pp. 519–524.
Duan, D–S. R. et. al., A Functional Soluble Extracellular Region of the Platelet–derived Growth Factor (PDGF) B–Receptor Antagonizes PDGF–stimulated Responses, (1991) J. Biol. Chem., 266, pp. 413–418.
Hoshi, H. and McKeehan, Brain– and liver cell–derived factors are required for growth of human endothelial cells in serum–free culture, (1984) Proc. Natl. Acad. Sci. U.S.A., 81 pp. 6413–6417.
Sanger et. al., DNA sequencing with chain–terminating inhibitors, (1977) P.N.A.S. USA, 74 pp. 5463–5467.
Feinberg, A.P. and Vogelstein, B., A. Technique for Radio-labeling DNA Restriction Endonuclease Fragments to High Specific Activity, (1983) Anal. Biochem., 132, pp. 6–13.
Hunter, W.M. and Greenwood, F.C., Preparation of Iodine–131 Labelled Human Growth Hormone of High Specific Activity, (1962) Nature (London), 194, pp. 495–496.
Scatchard, G., The Attractions Of Proteins For Small Molecules and Ions, (1949) Ann. N.Y. Acad. Sci., 51, pp. 660–672.
Bikflevi, A. et al., Interaction of Vasculotropin/Vascular Endothelial Cell Growth Factor With Human Umbilical Vein Endothelial Cells; Binding, Intemalization, Degradation, and Biological Effects, (1991) Journal of Cellular Physiology, 149, pp. 50–59.
Olsson, I. et al., The receptors for regulatory molecules of hematopoieses, (1992) Eur J. Haematol, 48 (1), pp. 1–9.

*Primary Examiner*—Stephen Walsh
*Assistant Examiner*—Nirmal S. Basi
*Attorney, Agent, or Firm*—J. Mark Hand; Jack L. Tribble

[57] ABSTRACT

The vascula endothelial cell growth factor (VEGF) inhibitors of the present invention are naturally occurring or recombinantly engineered soluble forms with or without a C-terminal transmembrane region of the receptor for VEGF, a very selective growth factor for endothelial cells. The soluble forms of the receptors will bind the growth factor with high affinity but do not result in signal transduction. These soluble forms of the receptor bind VEGF and inhibit its function.

4 Claims, 22 Drawing Sheets

```
GCGGACACTCCTCTCGGCTCCTCCCCGGAGCGGGGCTCGGAGCGGGCTCCGGGG
CTCGGGTGCAGCGGCCAGCGGCCTGGCGGCCTGGAGGATTACCCGGGGAAGTGGTTGTCTC
CTGGCTGGAGCCGCGAGAACGGGCGCTCAGGGCGGGGCGGGCGGCGGAACGAGAG
GACGGACTCTGCGGCCGGGTCGTTGGCCGGGGAGCGCGGGCACCGGGAGCGAGCAGGC
CGCGTCCGCGCTCACCATGGTCAGCTACTGGGACACCGGGGTCCTGCTGTGCGCGCTGCTC
AGCTGTCTGCTTCTCACAGGATCTAGTTCAGGTTCAGATTAAAGATCCTGAACTGAGTTTA
AAAGGCACCCAGCACACTCATGCAAGCAGGCCAGATCTCCAATGCAGGGGGAAG
CAGCCCATAAATGGTCTTTGCCTGATGGTGAGTAAGGAAGCGAAAGGCTGAGCATAACT
AAATCTGCCTGTGGAAGAAATGGCAAACAATTCTGCAGTACTTAACCTTGAACACAGCTCAA
GCAAACCACACTGGCTTCTACAGCTGCAAATATCTAGCTGTACTTACTTCAAGAAGAAGGA
AACAGAATCTGCAATCTATATATTATTAGTAGTAGACAGGTAGACCTTTCGTAGAGATGTACAG
TGAAATCCCGGACAGTAGAACATGACTGAAGGAAGGAGCTCGTCATTCCCTGCCGGGTTA
CGTCACCTAACATCACTGTTACTTAAAAAAGTTTCCACTTGACACTTTGATCCCTGATGGAA
AACGCATAATCTGGGACTAGAAAAGGGCTTCATCATCAAATGCAACGTACAAAGAAATA
GGGCTTCTGACCTGTGAAGCAACAGTCAATGGGCATTGTATAAGACAAACTATCTCACACA
TCGACAAACCAATACAATCATAGATGTCCAAATAAGCACACCCCAGTCAAATTACTTAG
AGGCCATACTCTGTCCTCAATTGTACTGCTACCACTCCCTTGAACACGAGAGTTCAAATGAC
CTGGAGTTACCCTGATGAAAAATAAGAGCTTCCGTAAGGCGAGAATTGACCAAGCA
ATTCCCATGCCAACAACATATTCTACAGTGTTCTTACTATTGACAAAATCTGTTAACACCTCAGTGCATA
GACTTTATACTTGTCGTGTAAGGAGTGGACCATCATCAAATCATGAAAACAGCAGGTGCATAGCT
TATATGATAAGCATTCATCACTGTGAAACATCGAAACAGCAGGTGCTTGAAACCGTAGCT
GGCAAGCGGTCTTACCGGCTCTCTATGAAAGTGAAGGCATTTCCCTGCCGGAAGTTGTAT
```

FIG. 2A

```
GGTTAAAGATGGGTTACCTGCGACTGAGAAATCTGCTCGCTATTTGACTCGTGGCTACTCG
TTAATTATCAAGGACGTAACTGAAGAGGATGCAGGAATTATACAATCTTGCTGAGCATAAAA
CAGTCAAATGTGTTAAAACCTCACTGCCACTCTAATTGTCAATGTGAAACCCAGATTTAC
GAAAGGCCGTGTCATCGTTCCAGACCCGGCTCTCTACCCACTGGGCAGCAGACAAATCC
TGACTTGTACCGCATATGGAAGCAAGGTGTATCCCTCAACCTAAGTGGTTCTGGCACCCTGTAAC
CATAATCATTCCGAAGCAAGGTGTGACAGAATTGAGAGCATCACTCAGCGCATGGCAATAATAGAAG
GCTGACAGCAACATGGGAAACAGAATTGAGAGCATCACTCAGCGCATGGCAATAATAGAAG
GAAGATAAGATGGCTAGCACCTTGGTTGTGGCTGACTCTAGAATTTCTGGAATCTACATT
GCATAGCTTCCAATAAAGTTGGGACTGTGGAAGAAACATAAGCTTTATATCACAGATGTG
CCAAATGGGTTTCATGTTAACTTGGAAATGCCGACGGAAGGAGACCTGAAACTGTC
TTGCACAGTTAACAAGTTCTTATACAGAGACGTTACTTGGATTTACTGCGGACAGTTAATAA
CAGAACAATGCACTACAGTATTAGCACAGTCAAAAAATGGCCATCAGGATTCAGGACACTCCATCA
CTCTTAATCTCTTACCATGACAGGGAAGAAATCCTCAGAAGAAGAATTACAATCAGAGGTGAGCAC
GGAATGTATACACAGGGAAGAAATCCTCCAAATTAAAAGCACAAGGAATGATTGTACC
TGCAACAAAAGGCTGTTTTCTCGGATCTCCAATTAAAAGTAACAGTTGTCTCATATCATCTTG
ACACAAGTAATGTAAAACATTAAAGGACTCATTAAAAGTAACAGTTGTCTCCCAAAATGAGTTCG
ATTTATTGTCACTGTTGCTAACTTTGCAGGCTCGGAGATGCTCTCCAGTCTCTGGGCCCCCATTCAGGCCG
GAGATGATAGCAGTAATAATGAGACCCCGGCTCCAGTCTCTGGGCCCCCATTCAGGCCG
AGGGGCTGCTCCGGGGGCGACTTGGTGCACGTTTGGATTTGGAGGATCCCTGCACTG
CCTTCTCTGTCTCTTGCTGTTTTCTCCTGCCTGATAAACAACAACTTGGGATGAT
CCTTTCCATTTGATGCCAACCTCTTTTATTTTAAGCGGCCCTATAGT
(SEQ. ID. NO.: 5)
```

FIG. 2B

MVSYWDTGVLLCALLSCLLLTGSSSGSKLKDPELSLKGTQHIMQAGQTLHLQC
RGEAAHKWSLPEMVSKESERLSITKSACGRNGKQFCSTLTNTAQANHTGFYS
CKYLAVPTSKKKETESAIYIFISDTGRPFVEMYSEIPEIIHMTEGRELVIPCRVTSP
NITVTLKKFPLDTLIPDGKRIIWDSRKGFIISNATYKEIGLLTCEATVNGHLYKTNYL
THRQTNTIIDVQISTPRPVKLLRGHTLVLNCTATTPLNTRVQMTWSYPDEKNKR
ASVRRRIDQSNSHANIFYSVLTIDKMQNKDKGLYTCRVRSGPSFKSVNTSVHIY
DKAFITVKHRKQQVLETVAGKRSYRLSMKVKAFPSPEVVWLKDGLPATEKSAR
YLTRGYSLIIKDVTEEDAGNYTILLSIKQSNVFKNLTATLIVNVKPQIYEKAVSSFP
DPALYPLGSRQILTCTAYGIPQPTIKWFWHPCNHNHSEARCDFCSNNEESFILD
ADSNMGNRIESITQRMAIIEGKNKMASTLVVADSRISGIYICIASNKVGTVGRNISF
YITDVPNGFHVNLEKMPTEGEDLKLSCTVNKFLYRDVTWILLRTVNNRTMHYSIS
KQKMAITKEHSITLNLTIMNVSLQDSGTYACRARNVYTGEEILQKKEITIRGEHCN
KKAVFSRISKFKSTRNDCTTQSNVKH (SEQ. ID. NO.: 6)

FIG. 3

```
GGTGGTGGTCGCTGCGTTTCCTCTGCCTGCGCGGGCATCACTTGCGCGCCGCAGAAAGTC
CGTCTGGCAGCCTGGATATCCTCTCCTACCGGCAGACGCGCTCCTGCAGCCCCTGCGCGGT
CGGCGCCGGGCTCCCTAGCCCTGTGCGCTCAACTGTCCTGCGCTGCGGGTGCCGCGAG
TCCACCTCCGCGCCTCCTTCTCTAGACAGGCGGCTCGGGAGAACAGGCTGCTGCCGAGTTC
CGGCATTTCGCCTCGCCCGGCTCGAGGTGCAGGATGCAGAGCAAGGTGCTGCTGCCGCCCT
GTGGCTCTGCGTGGAGACCCGGCCGCCTCTGTGGGTTTGCCTAGTGTTTCTCTTGATCTG
CCCAGGCTCAGCATACAAAAGAGACATACTTACAATTAAGGCTATACAACTCTTCAAATTACT
TGCAGGGGACAGAGGGACTTGGACTGGCTTTGGCCCAATAATCAGAGTGGCAGTGAGCAAA
GGGTGGAGGTGACTGAGTGCAGCGATGGCCTCTCTGTAAGACACTCACAATTCCAAAAGT
GATCGGAAATGACACTGGAGCCTACAAGTGCTTCTACCGGGAAACTGACTTGGCCTCGGTC
ATTTATGTCTATGTTCAAGATTACAGATCTCCATTATTGCTTCTGTTAGTGACCAACATGGAG
TCGTGTACATTACTGAGAACAAAAACAAACTGTGGTGATTCCATGTCTCGGTGTCCATTTCAA
ATCTCAACGTGTCACTTTGTGCAAGATACCCAGAGAAAGAGATTGTTCCTGATGGTAACAGAA
TTTCCTGGGACAGCAAGAAGGGCTTTACTATTCCCAGTACCAGTCAGATCAGCTATGCTGGCATG
GTCTTCTGTGAAGCAAAATTAATGATGAAAGTTACCAGTCGTCTGAGTCCATATCTCTATTATGTACATAGTTGTCGTT
GTAGGGTATAGGATTTATGATGTGGTTCTGAGTCCAAGAACTGACTTGAATTGAACTATCTGTTGGA
GAAAGCTTGTCTTAAATTGTACAGCAGCATAAGTGTGGGGATTGACTTCAACTGG
GAATACCCTTCTTCGAAGCATCAGCAGAAACTTGTAACCGAGAACCTAAAAACCCAGTCT
GGGAGTGAGATGAAGAAAATTTTGAGCACCTTAACTATAGATGGTGTAACCCGGAGTGACCA
```

FIG. 10A

```
AGGATTGTACACCTGTGCAGCATCCAGTGGGCTGATGACCAAGAAGAACAGCACATTTGTCA
GGGTCCATGAAAACCTTTGTTGCTTTGGAAGTGGCATGGAATCTCTGGTGGAAGCCACG
GTGGGGAGCGTGTCAGAATCCCTGCGAAGTACCTTGGTTACCACCCCAGAAATAAAAT
GGTATAAAATGGAATACCCCTTGAGTCCAATCACACAATTAAAGCGGGGCATGTACTGACG
ATTATGGAAGTGAGTGAAAGAGACACAGGAAATTACACTGTCATCCTTACCAATCCCATTCA
AAGGAGAAGCAGAGCCATGTCTCTGGTCTCTGGTGTATGTCCCCAGATTGGTGAGA
AATCTCTAATCTCTCTGTGGATTCCTACCAGTACGGCACCACTCAAACGCTGACATGTACG
GTCTATGCCATTCCTCCCCCGCATCACATCCACTGTATTGGCAGTTGGAGGAAGAGTGCG
CCAACGAGCCCAGCCAAGCTGTCTCAGTGACAAACCCATACCCTTGTGAAGAATCAATTGA
TGTGGAGGACTTCCAGGGAGGAAGAAACTGTAATAAAATCGCGTTAATAAAATCAATTGCTCTAATTGA
AGGAAAAACAAAACTGTAAGTACCCTTGTTATCCAAGCGGCAAATGTGTCAGCTTTGTACAA
ATGTGAAGCGGTCAACAAAGTTGCAACCTGACATGCAGCCCACTGAGACGGGTGTCTTTGTG
GGTCCTGAAATTACTTTGCAACAGATCTACGTTGAGAACCTCACTGTCAAGAACTTGGATACTCTTGTG
GTGCACTGCGACAGATCTGGGAGAGTTGCCCACACGTTGCAAGAACTTGGATACTCTTTGAAA
TGCCAATCCATGTGTCTCTAATAGCACAAATGACATTTGATCATGGAGCTTAAGAATGCA
TTGAATGCCACCATGTTCTCTAATAGCACAAATGACATTTGATCATGGAGCTTAAGAATGCA
TCCTTGCAGGACCAAGCACTATGTCTGCCTTGCTCAAGACAGGAAGACCAAGAAAAAGAC
ATTGCGTGGTGGTCAGGCAGCTCACAGTCCTAGAGCGTTAA    (SEQ. ID. NO.: 16)
```

FIG. 10B

Ser Glu Gln Asn Met Gln Ser Lys Val Leu Leu Ala Val Ala Leu Trp
1               5                       10                      15

Leu Cys Val Glu Thr Arg Ala Ala Ser Val Gly Leu Pro Ser Val Ser
            20                  25                  30

Leu Asp Leu Pro Arg Leu Ser Ile Gln Lys Asp Ile Leu Thr Ile Lys
            35                  40                  45

Ala Asn Thr Thr Leu Gln Ile Thr Cys Arg Gly Gln Arg Asp Leu Asp
        50                  55                  60

Trp Leu Trp Pro Asn Asn Gln Ser Gly Ser Glu Gln Arg Val Glu Val
65                  70                  75                      80

Thr Glu Cys Ser Asp Gly Leu Phe Cys Lys Thr Leu Thr Ile Pro Lys
                85                  90                  95

Val Ile Gly Asn Asp Thr Gly Ala Tyr Lys Cys Phe Tyr Arg Glu Thr
            100                 105                 110

Asp Leu Ala Ser Val Ile Tyr Val Tyr Val Gln Asp Tyr Arg Ser Pro
            115                 120                 125

Phe Ile Ala Ser Val Ser Asp Gln His Gly Val Val Tyr Ile Thr Glu
    130                 135                 140

Asn Lys Asn Lys Thr Val Val Ile Pro Cys Leu Gly Ser Ile Ser Asn
145                 150                 155                 160

Leu Asn Val Ser Leu Cys Ala Arg Tyr Pro Glu Lys Arg Phe Val Pro
                165                 170                 175

Asp Gly Asn Arg Ile Ser Trp Asp Ser Lys Lys Gly Phe Thr Ile Pro
            180                 185                 190

Ser Tyr Met Ile Ser Tyr Ala Gly Met Val Phe Cys Glu Ala Lys Ile
        195                 200                 205

Asn Asp Glu Ser Tyr Gln Ser Ile Met Tyr Ile Val Val Val Val Gly
        210                 215                 220

Tyr Arg Ile Tyr Asp Val Val Leu Ser Pro Ser His Gly Ile Glu Leu
225                 230                 235                 240

FIG.11A

Ser Val Gly Glu Lys Leu Val Leu Asn Cys Thr Ala Arg Thr Glu Leu
             245                 250                 255

Asn Val Gly Ile Asp Phe Asn Trp Glu Tyr Pro Ser Ser Lys His Gln
             260                 265                 270

His Lys Lys Leu Val Asn Arg Asp Leu Lys Thr Gln Ser Gly Ser Glu
         275                 280                 285

Met Lys Lys Phe Leu Ser Thr Leu Thr Ile Asp Gly Val Thr Arg Ser
     290                 295                 300

Asp Gln Gly Leu Tyr Thr Cys Ala Ala Ser Ser Gly Leu Met Thr Lys
305                 310                 315                 320

Lys Asn Ser Thr Phe Val Arg Val His Glu Lys Pro Phe Val Ala Phe
                 325                 330                 335

Gly Ser Gly Met Glu Ser Leu Val Glu Ala Thr Val Gly Glu Arg Val
             340                 345                 350

Arg Ile Pro Ala Lys Tyr Leu Gly Tyr Pro Pro Pro Glu Ile Lys Trp
             355                 360                 365

Tyr Lys Asn Gly Ile Pro Leu Glu Ser Asn His Thr Ile Lys Ala Gly
     370                 375                 380

His Val Leu Thr Ile Met Glu Val Ser Glu Arg Asp Thr Gly Asn Tyr
385                 390                 395                 400

Thr Val Ile Leu Thr Asn Pro Ile Ser Lys Glu Lys Gln Ser His Val
                 405                 410                 415

Val Ser Leu Val Val Tyr Val Pro Pro Gln Ile Gly Glu Lys Ser Leu
             420                 425                 430

Ile Ser Pro Val Asp Ser Tyr Gln Tyr Gly Thr Thr Gln Thr Leu Thr
         435                 440                 445

Cys Thr Val Tyr Ala Ile Pro Pro Pro His His Ile His Trp Tyr Trp
     450                 455                 460

FIG.11B

```
Gln Leu Glu Glu Glu Cys Ala Asn Glu Pro Ser Gln Ala Val Ser Val
465                 470                 475                 480

Thr Asn Pro Tyr Pro Cys Glu Glu Trp Arg Ser Val Glu Asp Phe Gln
                485                 490                 495

Gly Gly Asn Lys Ile Ala Val Asn Lys Asn Gln Phe Ala Leu Ile Glu
            500                 505                 510

Gly Lys Asn Lys Thr Val Ser Thr Leu Val Ile Gln Ala Ala Asn Val
            515                 520                 525

Ser Ala Leu Tyr Lys Cys Glu Ala Val Asn Lys Val Gly Arg Gly Glu
            530                 535                 540

Arg Val Ile Ser Phe His Val Thr Arg Gly Pro Glu Ile Thr Leu Gln
545                 550                 555                 560

Pro Asp Met Gln Pro Thr Glu Gln Glu Ser Val Ser Leu Trp Cys Thr
                565                 570                 575

Ala Asp Arg Ser Thr Phe Glu Asn Leu Thr Trp Tyr Lys Leu Gly Pro
            580                 585                 590

Gln Pro Leu Pro Ile His Val Gly Glu Leu Pro Thr Pro Val Cys Lys
            595                 600                 605

Asn Leu Asp Thr Leu Trp Lys Leu Asn Ala Thr Met Phe Ser Asn Ser
            610                 615                 620

Thr Asn Asp Ile Leu Ile Met Glu Leu Lys Asn Ala Ser Leu Gln Asp
625                 630                 635                 640

Gln Gly Asp Tyr Val Cys Leu Ala Gln Asp Arg Lys Thr Lys Lys Arg
                645                 650                 655

His Cys Val Val Arg Gln Leu Thr Val Leu Glu Arg    (SEQ ID NO. 13)
                660                 665
```

FIG.11C

| | |
|---|---|
| CTCGAGGTGC AGGATGCAGA GCAAGGTGCT GCTGGCCGTC GCCCTGTGGC TCTGCGTGGA | 60 |
| GACCCGGGCC GCCTCTGTGG GTTTGCCTAG TGTTTCTCTT GATCTGCCCA GGCTCAGCAT | 120 |
| ACAAAAAGAC ATACTTACAA TTAAGGCTAA TACAACTCTT CAAATTACTT GCAGGGGACA | 180 |
| GAGGGACTTG GACTGGCTTT GGCCCAATAA TCAGAGTGGC AGTGAGCAAA GGGTGGAGGT | 240 |
| GACTGAGTGC AGCGATGGCC TCTTCTGTAA GACACTCACA ATTCCAAAAG TGATCGGAAA | 300 |
| TGACACTGGA GCCTACAAGT GCTTCTACCG GGAAACTGAC TTGGCCTCGG TCATTTATGT | 360 |
| CTATGTTCAA GATTACAGAT CTCCATTTAT TGCTTCTGTT AGTGACCAAC ATGGAGTCGT | 420 |
| GTACATTACT GAGAACAAAA ACAAAACTGT GGTGATTCCA TGTCTCGGGT CCATTTCAAA | 480 |
| TCTCAACGTG TCACTTTGTG CAAGATACCC AGAAAAGAGA TTTGTTCCTG ATGGTAACAG | 540 |
| AATTTCCTGG GACAGCAAGA AGGGCTTTAC TATTCCCAGC TACATGATCA GCTATGCTGG | 600 |
| CATGGTCTTC TGTGAAGCAA AAATTAATGA TGAAAGTTAC CAGTCTATTA TGTACATAGT | 660 |
| TGTCGTTGTA GGGTATAGGA TTTATGATGT GGTTCTGAGT CCGTCTCATG GAATTGAACT | 720 |
| ATCTGTTGGA GAAAAGCTTG TCTTAAATTG TACAGCAAGA ACTGAACTAA ATGTGGGGAT | 780 |
| TGACTTCAAC TGGGAATACC CTTCTTCGAA GCATCAGCAT AAGAAACTTG TAAACCGAGA | 840 |
| CCTAAAAACC CAGTCTGGGA GTGAGATGAA GAAATTTTTG AGCACCTTAA CTATAGATGG | 900 |
| TGTAACCCGG AGTGACCAAG GATTGTACAC CTGTGCAGCA TCCAGTGGGC TGATGACCAA | 960 |
| GAAGAACAGC ACATTTGTCA GGGTCCATGA AAAACCTTTT GTTGCTTTTG GAAGTGGCAT | 1020 |
| GGAATCTCTG GTGGAAGCCA CGGTGGGGGA GCGTGTCAGA ATCCCTGCGA AGTACCTTGG | 1080 |
| TTACCCACCC CCAGAAATAA AATGGTATAA AAATGGAATA CCCCTTGAGT CCAATCACAC | 1140 |
| AATTAAAGCG GGGCATGTAC TGACGATTAT GGAAGTGAGT GAAAGAGACA CAGGAAATTA | 1200 |
| CACTGTCATC CTTACCAATC CCATTTCAAA GGAGAAGCAG AGCCATGTGG TCTCTCTGGT | 1260 |
| TGTGTATGTC CCACCCCAGA TTGGTGAGAA ATCTCTAATC TCTCCTGTGG ATTCCTACCA | 1320 |
| GTACGGCACC ACTCAAACGC TGACATGTAC GGTCTATGCC ATTCCTCCCC CGCATCACAT | 1380 |

FIG.12A

```
CCACTGGTAT TGGCAGTTGG AGGAAGAGTG CGCCAACGAG CCCAGCCAAG CTGTCTCAGT    1440

GACAAACCCA TACCCTTGTG AAGAATGGAG AAGTGTGGAG GACTTCCAGG GAGGAAATAA    1500

AATTGCCGTT AATAAAAATC AATTTGCTCT AATTGAAGGA AAAAACAAAA CTGTAAGTAC    1560

CCTTGTTATC CAAGCGGCAA ATGTGTCAGC TTTGTACAAA TGTGAAGCGG TCAACAAAGT    1620

CGGGAGAGGA GAGAGGGTGA TCTCCTTCCA CGTGACCAGG GGTCCTGAAA TTACTTTGCA    1680

ACCTGACATG CAGCCCACTG AGCAGGAGAG CGTGTCTTTG TGGTGCACTG CAGACAGATC    1740

TACGTTTGAG AACCTCACAT GGTACAAGCT TGGCCCACAG CCTCTGCCAA TCCATGTGGG    1800

AGAGTTGCCC ACACCTGTTT GCAAGAACTT GGATACTCTT TGGAAATTGA ATGCCACCAT    1860

GTTCTCTAAT AGCACAAATG ACATTTTGAT CATGGAGCTT AAGAATGCAT CCTTGCAGGA    1920

CCAAGGAGAC TATGTCTGCC TTGCTCAAGA CAGGAAGACC AAGAAAAGAC ATTGCGTGGT    1980

CAGGCAGCTC ACAGTCCTAG AGCGTGTGGC ACCCACGATC ACAGGAAACC TGGAGAATCA    2040

GACGACAAGT ATTGGGGAAA GCATCGAAGT CTCATGCACG GCATCTGGGA ATCCCCCTCC    2100

ACAGATCATG TGGTTTAAAG ATAATGAGAC CCTTGTAGAA GACTCAGGCA TTGTATTGAA    2160

GGATGGGAAC CGGAACCTCA CTATCCGCAG AGTGAGGAAG GAGGACGAAG GCCTCTACAC    2220

CTGCCAGGCA TGCAGTGTTC TTGGCTGTGC AAAAGTGGAG GCATTTTTCA TAATAGAAGG    2280

TGCCCAGGAA AAGACGAACT TGGAAATCAT TATTCTAGTA GGCACGACGG TGATTGCCAT    2340

GTTCTTCTGG CTACTTCTTG TCATCATCCT AGGGACCGTT TAA (SEQ ID NO. 18)     2383
```

FIG.12B

MQSKVLLAVALWLCVETRAASVGLPSVSLDLPRLSIQKDILTIKANTTLQITCRGQ
RDLDWLWPNNQSGSEQRVEVTECSDGLFCKTLTIPKVIGNDTGAYKCFYRETD
LASVIYVYVQDYRSPFIASVSDQHGVVYITENKNKTVVIPCLGSISNLNVSLCARY
PEKRFVPDGNRISWDSKKGFTIPSYMISYAGMVFCEAKINDESYQSIMYIVVVVG
YRIYDVVLSPSHGIELSVGEKLVLNCTARTELNVGIDFNWEYPSSKHQHKKLVN
RDLKTQSGSEMKKFLSTLTIDGVTRSDQGLYTCAASSGLMTKKNSTFVRVHEK
PFVAFGSGMESLVEATVGERVRIPAKYLGYPPPEIKWYKNGIPLESNHTIKAGHV
LTIMEVSERDTGNYTVILTNPISKEKQSHVVSLVVYVPPQIGEKSLISPVDSYQYG
TTQTLTCTVYAIPPPHHIHWYWQLEEECANEPSQAVSVTNPYPCEEWRSVEDF
QGGNKIAVNKNQFALIEGKNKTVSTLVIQAANVSALYKCEAVNKVGRGERVISFH
VTRGPEITLQPDMQPTEQESVSLWCTADRSTFENLTWYKLGPQPLPIHVGELPT
PVCKNLDTLWKLNATMFSNSTNDILIMELKNASLQDQGDYVCLAQDRKTKKRH
CVVRQLTVLERVAPTITGNLENQTTSIGESIEVSCTASGNPPPQIMWFKDNETLV
EDSGIVLKDGNRNLTIRRVRKEDEGLYTCQACSVLGCAKVEAFFIIEGAQEKTNL
EIIILVGTTVIAMFFWLLLVIILGTV⋯ (SEQ. ID. NO.: 15)

FIG. 13

```
GCGCTCACCATGGTCAGCTACTGGGACACCGGGGTCCTGCTGTGCCGCGCTGCTCAGCTGT
CTGCTTCTCACAGGATCTAGTTCAGGTTCAAATTAAAGATCCTGAACTGAGTTTAAAGGC
ACCCAGCACATCATGCAAGCAGGCCAGACACTCTCCAATGCAGGGGGAAGCAGCC
CATAAATGGTCTTTGCCTGAAATGGTGAGTAAGGAAGCGAAAGGCTGAGCATAACTAAATC
TGCCTGTGGAAGAAATGGCAAACAATTCTGCAGTACTTAACCTTGAACACAGCTCAAGCAA
ACCACACTGGCTTCTACAGCTGCAAATATCTAGCTGTACTTCAAGAAGAGGAAACA
GAATCTGCAATCTATATATTATTAGTGATACAGGTAGACCTTTCGTAGAGATGTACAGTGAA
ATCCCCGAAATTATACACATGACTGAAGGAGGAGCTCGTCATTCCCTGCCGGGTTACGTC
ACCTAACATCGTTACTTAAAAAGTTCCACTTGACACTTGATCCCTGATGGAAACG
CATAATCTGGGACAGTAGAAAGGGCTTCATCATCAAATGCAACGTACAAAGAAATAGGGC
TTCTGACCTGTGAAGCAACAGTGCATTTGTATAAGACAAACTATCTCACACATCGAC
AACCAATACAATCATAGATGTCCAAATAAGCACACGCCCAGTCAAATTACTTAGAGGC
CATATCTCTTGTCTCAATTGTACTGTACCACTCCCTTGAACACGAGAGTTCAAATGACCTGG
AGTTACCCTGATGAAAAATAAGAGAGCTTCCGTAAGGCGACGAATTGACCAAGCAATTC
CCATGCCAACATATTCTACAGTGTTCTTACTATTGACAAATGCAGAACAAAGAACAAAGGACT
TTATACTTGTCGTAAGGAGTGGACCATCAATCATTCAAATCTGTTAACACCTCAGTGCATATATA
TGATAAAGCATTCACTGCTCTCACTGTGAAACATCGAAAACAGCAGGTGCTTGAAACCGTAGCTGGCA
AGCGGTCTTACCGGCTCATCCGGCTATTCCCGCCGGAAGTTGTATGTTA
AAGATGGGTTACCTGCGACTGAGAAATCTGCTCGCTATTTGACTCGTCGTTAAT
```

FIG. 14A

```
TATCAAGGACGTAACTGAAGAGGATGCAGGGAATTATACAATCTTGCTGAGCATAAAACAGT
CAAATGTGTTAAAACCTCACTGCCACTCTAATTGTCAATGTGAAACCCAGATTACGAAA
AGGCCGTGTCATCGTGTTCCAGACCCACTGGCTCTCTACCCACTGGGCAGACAAATCCTGAC
TTGTACCGCATATGGTATCCCTCAACCTACAAGTGGTTCTGGCACCCCTGTAACCATAA
TCATTCCGAAGCAAGGTGTGACTTTTGTTCCAATAATGAAGAGTCCTTTATCCTGGATGCTGA
CAGCAACATGGGAAACAGAATTGAGAGCATCAGCGCATGGCAATAATAGAAGGAAAG
AATAAGATGGCTAGCAAGTTGGGACTTGGTTGTGTGGGAAGAAACATAAGCTTTTATCACAGATGTGCCAAAT
GCTTCCAATAAAGTTGGGACTGTGGAAAAAATGCCGACGGAGGACCTGAACTGTCTTGCAC
GGGTTTCATGTTAACTTGTATACAGAGACGTTACTTGGATTTACTGCGGACAGTTAATAACAGAAC
AGTTAACAAGTTCTACAGTATTAGCAAGCAAAAAATGGCCATCACTAAGGAGCACTCACTCTTAA
AATGCACTACAGTATTAGCAAGCAAAAAATGGCCATCACTAAGGAGCACTCACTCTTAA
TCTTACCATCATGAATGTTCCCTGCAAGATTCAGGCACCTATGCCTGCAGAGCCAGGAATG
TATACAGGGGAAGAAATCCTCCAGAAGAAAGAATTACAATCAGAGATCAGGAAGCACCA
TACCTCCTGCGAAACCTCAGTGATCACACAGTGGCCATCAGCAGTTCCACCACTTAGACTG
TCATGCTAATGGTGTCCCCGAGCCTCAGATCACTTGGTTTAAAACAACCACAAAATACAACA
AGAGCCTGGAATATTTAGGACCAGGAAGCAGCACGCTGTTTATTGAAAGAGTCACAGAAG
AGGATGAAGGTGTCTATCACTGCAAGAAGCAGCACCAACCAGAAGGGCTCTGTGAAAGTTCAGC
ATACCTCACTGTTCAAGGAACCTCGACAAGTCTAATCTGTGAGCTGATCACTCTAACATGCA
CCTGTGTGGCTGCGACTCTCTTCTGGCTCCTATTAACCCTCCTTATCTAA (SEQ. ID. NO.: 17)
```

FIG. 14B

MVSYWDTGVLLCALLSCLLLTGSSSGSKLKDPELSLKGTQHIMQAGQTLHLQC
RGEAAHKWSLPEMVSKESERLSITKSACGRNGKQFCSTLTLNTAQANHTGFYS
CKYLAVPTSKKKETESAIYIFISDTGRPFVEMYSEIPEIIHMTEGRELVIPCRVTSP
NITVTLKKFPLDTLIPDGKRIIWDSRKGFIISNATYKEIGLLTCEATVNGHLYKTNYL
THRQTNTIIDVQISTPRPVKLLRGHTLVLNCTATTPLNTRVQMTWSYPDEKNKR
ASVRRRIDQSNSHANIFYSVLTIDKMQNKDKGLYTCRVRSGPSFKSVNTSVHIY
DKAFITVKHRKQQVLETVAGKRSYRLSMKVKAFPSPEVVWLKDGLPATEKSAR
YLTRGYSLIIKDVTEEDAGNYTILLSIKQSNVFKNLTATLIVNVKPQIYEKAVSSFP
DPALYPLGSRQILTCTAYGIPQPTIKWFWHPCNHNHSEARCDFCSNNEESFILD
ADSNMGNRIESITQRMAIIEGKNKMASTLVVADSRISGIYICIASNKVGTVGRNISF
YITDVPNGFHVNLEKMPTEGEDLKLSCTVNKFLYRDVTWILLRTVNNRTMHYSIS
KQKMAITKEHSITLNLTIMNVSLQDSGTYACRARNVYTGEEILQKKEITIRDQEAP
YLLRNLSDHTVAISSSTTLDCHANGVPEPQITWFKNNHKIQQEPGIILGPGSSTLF
IERVTEEDEGVYHCKATNQKGSVESSAYLTVQGTSDKSNLELITLTCTCVAATLF
WLLLTLLI  (SEQ. ID. NO.:14)

FIG. 15

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GCACCTTGGT TGTGGCTGAC                                         20

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

TGGAATTCGT GCTGCTTCCT GGTCC                                   25

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GGAATTCCGC GCTCACCATG GTCAGC                                  26

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

TTTGAATTCA CCCGGCAGGG AATGACG                                 27

( 2 ) INFORMATION FOR SEQ ID NO:5:

( i ) SEQUENCE CHARACTERISTICS:
        ( A ) LENGTH: 2651 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
GCGGACACTC  CTCTCGGCTC  CTCCCCGGCA  GCGGCGGCGG  CTCGGAGCGG  GCTCCGGGGC    60
TCGGGTGCAG  CGGCCAGCGG  GCCTGGCGGC  GAGGATTACC  CGGGGAAGTG  GTTGTCTCCT   120
GGCTGGAGCC  GCGAGACGGG  CGCTCAGGGC  GCGGGGCCGG  CGGCGGCGAA  CGAGAGGACG   180
GACTCTGGCG  GCCGGGTCGT  TGGCCGGGGG  AGCGCGGGCA  CCGGGCGAGC  AGGCCGCGTC   240
GCGCTCACCA  TGGTCAGCTA  CTGGGACACC  GGGGTCCTGC  TGTGCGCGCT  GCTCAGCTGT   300
CTGCTTCTCA  CAGGATCTAG  TTCAGGTTCA  AAATTAAAAG  ATCCTGAACT  GAGTTTAAAA   360
GGCACCCAGC  ACATCATGCA  AGCAGGCCAG  ACACTGCATC  TCCAATGCAG  GGGGGAAGCA   420
GCCCATAAAT  GGTCTTTGCC  TGAAATGGTG  AGTAAGGAAA  GCGAAAGGCT  GAGCATAACT   480
AAATCTGCCT  GTGGAAGAAA  TGGCAAACAA  TTCTGCAGTA  CTTTAACCTT  GAACACAGCT   540
CAAGCAAACC  ACACTGGCTT  CTACAGCTGC  AAATATCTAG  CTGTACCTAC  TTCAAAGAAG   600
AAGGAAACAG  AATCTGCAAT  CTATATATTT  ATTAGTGATA  CAGGTAGACC  TTTCGTAGAG   660
ATGTACAGTG  AAATCCCCGA  AATTATACAC  ATGACTGAAG  GAAGGGAGCT  CGTCATTCCC   720
TGCCGGGTTA  CGTCACCTAA  CATCACTGTT  ACTTTAAAAA  AGTTTCCACT  TGACACTTTG   780
ATCCCTGATG  GAAAACGCAT  AATCTGGGAC  AGTAGAAAGG  GCTTCATCAT  ATCAAATGCA   840
ACGTACAAAG  AAATAGGGCT  TCTGACCTGT  GAAGCAACAG  TCAATGGGCA  TTTGTATAAG   900
ACAAACTATC  TCACACATCG  ACAAACCAAT  ACAATCATAG  ATGTCCAAAT  AAGCACACCA   960
CGCCCAGTCA  AATTACTTAG  AGGCCATACT  CTTGTCCTCA  ATTGTACTGC  TACCACTCCC  1020
TTGAACACGA  GAGTTCAAAT  GACCTGGAGT  TACCCTGATG  AAAAAAATAA  GAGAGCTTCC  1080
GTAAGGCGAC  GAATTGACCA  AAGCAATTCC  CATGCCAACA  TATTCTACAG  TGTTCTTACT  1140
ATTGACAAAA  TGCAGAACAA  AGACAAAGGA  CTTTATACTT  GTCGTGTAAG  GAGTGGACCA  1200
TCATTCAAAT  CTGTTAACAC  CTCAGTGCAT  ATATATGATA  AAGCATTCAT  CACTGTGAAA  1260
CATCGAAAAC  AGCAGGTGCT  TGAAACCGTA  GCTGGCAAGC  GGTCTTACCG  GCTCTCTATG  1320
AAAGTGAAGG  CATTTCCCTC  GCCGGAAGTT  GTATGGTTAA  AGATGGGTT   ACCTGCGACT  1380
GAGAAATCTG  CTCGCTATTT  GACTCGTGGC  TACTCGTTAA  TTATCAAGGA  CGTAACTGAA  1440
GAGGATGCAG  GGAATTATAC  AATCTTGCTG  AGCATAAAAC  AGTCAAATGT  GTTTAAAAAC  1500
CTCACTGCCA  CTCTAATTGT  CAATGTGAAA  CCCCAGATTT  ACGAAAAGGC  CGTGTCATCG  1560
TTTCCAGACC  CGGCTCTCTA  CCCACTGGGC  AGCAGACAAA  TCCTGACTTG  TACCGCATAT  1620
GGTATCCCTC  AACCTACAAT  CAAGTGGTTC  TGGCACCCCT  GTAACCATAA  TCATTCCGAA  1680
GCAAGGTGTG  ACTTTTGTTC  CAATAATGAA  GAGTCCTTTA  TCCTGGATGC  TGACAGCAAC  1740
ATGGGAAACA  GAATTGAGAG  CATCACTCAG  CGCATGGCAA  TAATAGAAGG  AAAGAATAAG  1800
ATGGCTAGCA  CCTTGGTTGT  GGCTGACTCT  AGAATTTCTG  GAATCTACAT  TTGCATAGCT  1860
TCCAATAAAG  TTGGGACTGT  GGGAAGAAAC  ATAAGCTTTT  ATATCACAGA  TGTGCCAAAT  1920
GGGTTTCATG  TTAACTTGGA  AAAAATGCCG  ACGGAAGGAG  AGGACCTGAA  ACTGTCTTGC  1980
ACAGTTAACA  AGTTCTTATA  CAGAGACGTT  ACTTGGATTT  TACTGCGGAC  AGTTAATAAC  2040
AGAACAATGC  ACTACAGTAT  TAGCAAGCAA  AAAATGGCCA  TCACTAAGGA  GCACTCCATC  2100
ACTCTTAATC  TTACCATCAT  GAATGTTTCC  CTGCAAGATT  CAGGCACCTA  TGCCTGCAGA  2160
GCCAGGAATG  TATACACAGG  GGAAGAAATC  CTCCAGAAGA  AAGAAATTAC  AATCAGAGGT  2220
GAGCACTGCA  ACAAAAGGGC  TGTTTTCTCT  CGGATCTCCA  AATTTAAAAG  CACAAGGAAT  2280
```

-continued

```
GATTGTACCA CACAAAGTAA TGTAAAACAT TAAAGGACTC ATTAAAAAGT AACAGTTGTC    2340

TCATATCATC TTGATTTATT GTCACTGTTG CTAACTTTCA GGCTCGGAGG AGATGCTCCT    2400

CCCAAAATGA GTTCGGAGAT GATAGCAGTA ATAATGAGAC CCCCGGGCTC CAGCTCTGGG    2460

CCCCCCATTC AGGCCGAGGG GGCTGCTCCG GGGGGCCGAC TTGGTGCACG TTTGGATTTG    2520

GAGGATCCCT GCACTGCCTT CTCTGTGTTT GTTGCTCTTG CTGTTTTCTC CTGCCTGATA    2580

AACAACAACT TGGGATGATC CTTTCCATTT TGATGCCAAC CTCTTTTTAT TTTTAAGCGG    2640

CGCCCTATAG T                                                         2651
```

( 2 ) INFORMATION FOR SEQ ID NO:6:

( i ) SEQUENCE CHARACTERISTICS:
        ( A ) LENGTH: 687 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
```

|       |     |     |     |     |     | 275 |     |     |     |     |     | 280 |     |     |     |     |     | 285 |     |
|-------|-----|-----|-----|-----|-----|-----|-----|-----|-----|-----|-----|-----|-----|-----|-----|-----|-----|-----|-----|

Ala Asn Ile Phe Tyr Ser Val Leu Thr Ile Asp Lys Met Gln Asn Lys
    290                    295                    300

Asp Lys Gly Leu Tyr Thr Cys Arg Val Arg Ser Gly Pro Ser Phe Lys
305                    310                    315                    320

Ser Val Asn Thr Ser Val His Ile Tyr Asp Lys Ala Phe Ile Thr Val
                325                    330                    335

Lys His Arg Lys Gln Gln Val Leu Glu Thr Val Ala Gly Lys Arg Ser
            340                    345                  350

Tyr Arg Leu Ser Met Lys Val Lys Ala Phe Pro Ser Pro Glu Val Val
        355                  360                  365

Trp Leu Lys Asp Gly Leu Pro Ala Thr Glu Lys Ser Ala Arg Tyr Leu
    370                  375                    380

Thr Arg Gly Tyr Ser Leu Ile Ile Lys Asp Val Thr Glu Glu Asp Ala
385                    390                    395                    400

Gly Asn Tyr Thr Ile Leu Leu Ser Ile Lys Gln Ser Asn Val Phe Lys
                405                    410                  415

Asn Leu Thr Ala Thr Leu Ile Val Asn Val Lys Pro Gln Ile Tyr Glu
            420                    425                  430

Lys Ala Val Ser Ser Phe Pro Asp Pro Ala Leu Tyr Pro Leu Gly Ser
        435                  440                  445

Arg Gln Ile Leu Thr Cys Thr Ala Tyr Gly Ile Pro Gln Pro Thr Ile
    450                  455                    460

Lys Trp Phe Trp His Pro Cys Asn His Asn His Ser Glu Ala Arg Cys
465                    470                    475                    480

Asp Phe Cys Ser Asn Asn Glu Glu Ser Phe Ile Leu Asp Ala Asp Ser
                485                    490                  495

Asn Met Gly Asn Arg Ile Glu Ser Ile Thr Gln Arg Met Ala Ile Ile
            500                    505                  510

Glu Gly Lys Asn Lys Met Ala Ser Thr Leu Val Val Ala Asp Ser Arg
        515                  520                  525

Ile Ser Gly Ile Tyr Ile Cys Ile Ala Ser Asn Lys Val Gly Thr Val
    530                  535                    540

Gly Arg Asn Ile Ser Phe Tyr Ile Thr Asp Val Pro Asn Gly Phe His
545                    550                    555                    560

Val Asn Leu Glu Lys Met Pro Thr Glu Gly Glu Asp Leu Lys Leu Ser
                565                    570                  575

Cys Thr Val Asn Lys Phe Leu Tyr Arg Asp Val Thr Trp Ile Leu Leu
            580                    585                  590

Arg Thr Val Asn Asn Arg Thr Met His Tyr Ser Ile Ser Lys Gln Lys
        595                  600                  605

Met Ala Ile Thr Lys Glu His Ser Ile Thr Leu Asn Leu Thr Ile Met
610                    615                    620

Asn Val Ser Leu Gln Asp Ser Gly Thr Tyr Ala Cys Arg Ala Arg Asn
625                    630                    635                    640

Val Tyr Thr Gly Glu Glu Ile Leu Gln Lys Lys Glu Ile Thr Ile Arg
                645                    650                  655

Gly Glu His Cys Asn Lys Lys Ala Val Phe Ser Arg Ile Ser Lys Phe
            660                    665                  670

Lys Ser Thr Arg Asn Asp Cys Thr Thr Gln Ser Asn Val Lys His
        675                  680                  685

( 2 ) INFORMATION FOR SEQ ID NO:7:

( i ) SEQUENCE CHARACTERISTICS:
  ( A ) LENGTH: 37 base pairs
  ( B ) TYPE: nucleic acid
  ( C ) STRANDEDNESS: single
  ( D ) TOPOLOGY: linear ( i i ) MOLECULE TYPE: Genomic DNA ( x i ) SEQUENCE DESCRIPTION: SEQ ID NO:7:

TTTTGGATCC CTGCAGACAG ATCTACGTTT GAGAACC     37

( 2 ) INFORMATION FOR SEQ ID NO:8:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:8:

TTTTGGATCC TTAACGCTCT AGGACTGTGA GC     32

( 2 ) INFORMATION FOR SEQ ID NO:9:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:9:

TTTTGGATCC AACGGTCCCT AGGATGATGA C     31

( 2 ) INFORMATION FOR SEQ ID NO:10:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:10:

AGCACCTTGG TTGTGGCTGA CTC     23

( 2 ) INFORMATION FOR SEQ ID NO:11:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: Genomic DNA ( x i ) SEQUENCE DESCRIPTION: SEQ ID NO:11:

TTTTGGATCC TTAGATAAGG AGGGTTAATA GG     32

( 2 ) INFORMATION FOR SEQ ID NO:12:

( i ) SEQUENCE CHARACTERISTICS:
    ( A ) LENGTH: 661 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:12:

| Ser | Lys | Leu | Lys | Asp | Pro | Glu | Leu | Ser | Leu | Lys | Gly | Thr | Gln | His | Ile |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Met | Gln | Ala | Gly | Gln | Thr | Leu | His | Leu | Gln | Cys | Arg | Gly | Glu | Ala | Ala |
|     |     |     | 20  |     |     |     |     | 25  |     |     |     | 30  |     |     |     |
| His | Lys | Trp | Ser | Leu | Pro | Glu | Met | Val | Ser | Lys | Glu | Ser | Glu | Arg | Leu |
|     |     | 35  |     |     |     | 40  |     |     |     | 45  |     |     |     |     |     |
| Ser | Ile | Thr | Lys | Ser | Ala | Cys | Gly | Arg | Asn | Gly | Lys | Gln | Phe | Cys | Ser |
|     | 50  |     |     |     |     | 55  |     |     |     |     | 60  |     |     |     |     |
| Thr | Leu | Thr | Leu | Asn | Thr | Ala | Gln | Ala | Asn | His | Thr | Gly | Phe | Tyr | Ser |
| 65  |     |     |     |     | 70  |     |     |     |     | 75  |     |     |     |     | 80  |
| Cys | Lys | Tyr | Leu | Ala | Val | Pro | Thr | Ser | Lys | Lys | Lys | Glu | Thr | Glu | Ser |
|     |     |     |     | 85  |     |     |     |     | 90  |     |     |     |     | 95  |     |
| Ala | Ile | Tyr | Ile | Phe | Ile | Ser | Asp | Thr | Gly | Arg | Pro | Phe | Val | Glu | Met |
|     |     |     | 100 |     |     |     |     | 105 |     |     |     |     | 110 |     |     |
| Tyr | Ser | Glu | Ile | Pro | Glu | Ile | Ile | His | Met | Thr | Glu | Gly | Arg | Glu | Leu |
|     |     | 115 |     |     |     |     | 120 |     |     |     |     | 125 |     |     |     |
| Val | Ile | Pro | Cys | Arg | Val | Thr | Ser | Pro | Asn | Ile | Thr | Val | Thr | Leu | Lys |
|     | 130 |     |     |     |     | 135 |     |     |     |     | 140 |     |     |     |     |
| Lys | Phe | Pro | Leu | Asp | Thr | Leu | Ile | Pro | Asp | Gly | Lys | Arg | Ile | Ile | Trp |
| 145 |     |     |     |     | 150 |     |     |     |     | 155 |     |     |     |     | 160 |
| Asp | Ser | Arg | Lys | Gly | Phe | Ile | Ile | Ser | Asn | Ala | Thr | Tyr | Lys | Glu | Ile |
|     |     |     |     | 165 |     |     |     |     | 170 |     |     |     |     | 175 |     |
| Gly | Leu | Leu | Thr | Cys | Glu | Ala | Thr | Val | Asn | Gly | His | Leu | Tyr | Lys | Thr |
|     |     |     | 180 |     |     |     |     | 185 |     |     |     |     | 190 |     |     |
| Asn | Tyr | Leu | Thr | His | Arg | Gln | Thr | Asn | Thr | Ile | Ile | Asp | Val | Gln | Ile |
|     |     | 195 |     |     |     |     | 200 |     |     |     |     | 205 |     |     |     |
| Ser | Thr | Pro | Arg | Pro | Val | Lys | Leu | Leu | Arg | Gly | His | Thr | Leu | Val | Leu |
|     | 210 |     |     |     |     | 215 |     |     |     |     | 220 |     |     |     |     |
| Asn | Cys | Thr | Ala | Thr | Thr | Pro | Leu | Asn | Thr | Arg | Val | Gln | Met | Thr | Trp |
| 225 |     |     |     |     | 230 |     |     |     |     | 235 |     |     |     |     | 240 |
| Ser | Tyr | Pro | Asp | Glu | Lys | Asn | Lys | Arg | Ala | Ser | Val | Arg | Arg | Arg | Ile |
|     |     |     |     | 245 |     |     |     |     | 250 |     |     |     |     | 255 |     |
| Asp | Gln | Ser | Asn | Ser | His | Ala | Asn | Ile | Phe | Tyr | Ser | Val | Leu | Thr | Ile |
|     |     |     | 260 |     |     |     |     | 265 |     |     |     |     | 270 |     |     |
| Asp | Lys | Met | Gln | Asn | Lys | Asp | Lys | Gly | Leu | Tyr | Thr | Cys | Arg | Val | Arg |
|     |     | 275 |     |     |     |     | 280 |     |     |     |     | 285 |     |     |     |
| Ser | Gly | Pro | Ser | Phe | Lys | Ser | Val | Asn | Thr | Ser | Val | His | Ile | Tyr | Asp |
|     | 290 |     |     |     |     | 295 |     |     |     |     | 300 |     |     |     |     |
| Lys | Ala | Phe | Ile | Thr | Val | Lys | His | Arg | Lys | Gln | Gln | Val | Leu | Glu | Thr |
| 305 |     |     |     |     | 310 |     |     |     |     | 315 |     |     |     |     | 320 |
| Val | Ala | Gly | Lys | Arg | Ser | Tyr | Arg | Leu | Ser | Met | Lys | Val | Lys | Ala | Phe |
|     |     |     |     | 325 |     |     |     |     | 330 |     |     |     |     | 335 |     |
| Pro | Ser | Pro | Glu | Val | Val | Trp | Leu | Lys | Asp | Gly | Leu | Pro | Ala | Thr | Glu |
|     |     |     | 340 |     |     |     |     | 345 |     |     |     |     | 350 |     |     |
| Lys | Ser | Ala | Arg | Tyr | Leu | Thr | Arg | Gly | Tyr | Ser | Leu | Ile | Ile | Lys | Asp |
|     |     | 355 |     |     |     |     | 360 |     |     |     |     | 365 |     |     |     |
| Val | Thr | Glu | Glu | Asp | Ala | Gly | Asn | Tyr | Thr | Ile | Leu | Leu | Ser | Ile | Lys |
|     | 370 |     |     |     |     | 375 |     |     |     |     | 380 |     |     |     |     |
| Gln | Ser | Asn | Val | Phe | Lys | Asn | Leu | Thr | Ala | Thr | Leu | Ile | Val | Asn | Val |
| 385 |     |     |     |     | 390 |     |     |     |     | 395 |     |     |     |     | 400 |

-continued

| | | | | | | | | | | | | | | | |
|---|---|---|---|---|---|---|---|---|---|---|---|---|---|---|---|
| Lys | Pro | Gln | Ile | Tyr | Glu | Lys | Ala | Val | Ser | Ser | Phe | Pro | Asp | Pro | Ala |
| | | | | 405 | | | | 410 | | | | | | 415 | |
| Leu | Tyr | Pro | Leu | Gly | Ser | Arg | Gln | Ile | Leu | Thr | Cys | Thr | Ala | Tyr | Gly |
| | | | 420 | | | | | 425 | | | | | 430 | | |
| Ile | Pro | Gln | Pro | Thr | Ile | Lys | Trp | Phe | Trp | His | Pro | Cys | Asn | His | Asn |
| | | | 435 | | | | | 440 | | | | | 445 | | |
| His | Ser | Glu | Ala | Arg | Cys | Asp | Phe | Cys | Ser | Asn | Asn | Glu | Glu | Ser | Phe |
| | | | 450 | | | | 455 | | | | | 460 | | | |
| Ile | Leu | Asp | Ala | Asp | Ser | Asn | Met | Gly | Asn | Arg | Ile | Glu | Ser | Ile | Thr |
| 465 | | | | | 470 | | | | | 475 | | | | | 480 |
| Gln | Arg | Met | Ala | Ile | Ile | Glu | Gly | Lys | Asn | Lys | Met | Ala | Ser | Thr | Leu |
| | | | | 485 | | | | | 490 | | | | | 495 | |
| Val | Val | Ala | Asp | Ser | Arg | Ile | Ser | Gly | Ile | Tyr | Ile | Cys | Ile | Ala | Ser |
| | | | 500 | | | | | 505 | | | | | 510 | | |
| Asn | Lys | Val | Gly | Thr | Val | Gly | Arg | Asn | Ile | Ser | Phe | Tyr | Ile | Thr | Asp |
| | | | 515 | | | | 520 | | | | | 525 | | | |
| Val | Pro | Asn | Gly | Phe | His | Val | Asn | Leu | Glu | Lys | Met | Pro | Thr | Glu | Gly |
| | 530 | | | | | 535 | | | | | 540 | | | | |
| Glu | Asp | Leu | Lys | Leu | Ser | Cys | Thr | Val | Asn | Lys | Phe | Leu | Tyr | Arg | Asp |
| 545 | | | | | 550 | | | | | 555 | | | | | 560 |
| Val | Thr | Trp | Ile | Leu | Leu | Arg | Thr | Val | Asn | Asn | Arg | Thr | Met | His | Tyr |
| | | | | 565 | | | | | 570 | | | | | 575 | |
| Ser | Ile | Ser | Lys | Gln | Lys | Met | Ala | Ile | Thr | Lys | Glu | His | Ser | Ile | Thr |
| | | | 580 | | | | | 585 | | | | | 590 | | |
| Leu | Asn | Leu | Thr | Ile | Met | Asn | Val | Ser | Leu | Gln | Asp | Ser | Gly | Thr | Tyr |
| | | | 595 | | | | 600 | | | | | 605 | | | |
| Ala | Cys | Arg | Ala | Arg | Asn | Val | Tyr | Thr | Gly | Glu | Glu | Ile | Leu | Gln | Lys |
| | 610 | | | | | 615 | | | | | 620 | | | | |
| Lys | Glu | Ile | Thr | Ile | Arg | Gly | Glu | His | Cys | Asn | Lys | Lys | Ala | Val | Phe |
| 625 | | | | | 630 | | | | | 635 | | | | | 640 |
| Ser | Arg | Ile | Ser | Lys | Phe | Lys | Ser | Thr | Arg | Asn | Asp | Cys | Thr | Thr | Gln |
| | | | | 645 | | | | | 650 | | | | | 655 | |
| Ser | Asn | Val | Lys | His | | | | | | | | | | | |
| | | | 660 | | | | | | | | | | | | |

( 2 ) INFORMATION FOR SEQ ID NO:13:

( i ) SEQUENCE CHARACTERISTICS:
        ( A ) LENGTH: 668 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:13:

| | | | | | | | | | | | | | | | |
|---|---|---|---|---|---|---|---|---|---|---|---|---|---|---|---|
| Ser | Glu | Gln | Asn | Met | Gln | Ser | Lys | Val | Leu | Leu | Ala | Val | Ala | Leu | Trp |
| 1 | | | | 5 | | | | | 10 | | | | | 15 | |
| Leu | Cys | Val | Glu | Thr | Arg | Ala | Ala | Ser | Val | Gly | Leu | Pro | Ser | Val | Ser |
| | | | 20 | | | | | 25 | | | | | 30 | | |
| Leu | Asp | Leu | Pro | Arg | Leu | Ser | Ile | Gln | Lys | Asp | Ile | Leu | Thr | Ile | Lys |
| | | | 35 | | | | 40 | | | | | 45 | | | |
| Ala | Asn | Thr | Thr | Leu | Gln | Ile | Thr | Cys | Arg | Gly | Gln | Arg | Asp | Leu | Asp |
| | | 50 | | | | | 55 | | | | | 60 | | | |
| Trp | Leu | Trp | Pro | Asn | Asn | Gln | Ser | Gly | Ser | Glu | Gln | Arg | Val | Glu | Val |
| 65 | | | | | 70 | | | | | 75 | | | | | 80 |
| Thr | Glu | Cys | Ser | Asp | Gly | Leu | Phe | Cys | Lys | Thr | Leu | Thr | Ile | Pro | Lys |

-continued

```
                              85                         90                          95
     Val   Ile   Gly   Asn   Asp   Thr   Gly   Ala   Tyr   Lys   Cys   Phe   Tyr   Arg   Glu   Thr
                             100                        105                         110
     Asp   Leu   Ala   Ser   Val   Ile   Tyr   Val   Tyr   Val   Gln   Asp   Tyr   Arg   Ser   Pro
                             115                        120                         125
     Phe   Ile   Ala   Ser   Val   Ser   Asp   Gln   His   Gly   Val   Val   Tyr   Ile   Thr   Glu
                             130                        135                         140
     Asn   Lys   Asn   Lys   Thr   Val   Val   Ile   Pro   Cys   Leu   Gly   Ser   Ile   Ser   Asn
     145                                 150                        155                         160
     Leu   Asn   Val   Ser   Leu   Cys   Ala   Arg   Tyr   Pro   Glu   Lys   Arg   Phe   Val   Pro
                             165                        170                         175
     Asp   Gly   Asn   Arg   Ile   Ser   Trp   Asp   Ser   Lys   Lys   Gly   Phe   Thr   Ile   Pro
                             180                        185                         190
     Ser   Tyr   Met   Ile   Ser   Tyr   Ala   Gly   Met   Val   Phe   Cys   Glu   Ala   Lys   Ile
                             195                        200                         205
     Asn   Asp   Glu   Ser   Tyr   Gln   Ser   Ile   Met   Tyr   Ile   Val   Val   Val   Val   Gly
     210                                 215                        220
     Tyr   Arg   Ile   Tyr   Asp   Val   Val   Leu   Ser   Pro   Ser   His   Gly   Ile   Glu   Leu
     225                                 230                        235                         240
     Ser   Val   Gly   Glu   Lys   Leu   Val   Leu   Asn   Cys   Thr   Ala   Arg   Thr   Glu   Leu
                             245                        250                         255
     Asn   Val   Gly   Ile   Asp   Phe   Asn   Trp   Glu   Tyr   Pro   Ser   Ser   Lys   His   Gln
                             260                        265                         270
     His   Lys   Lys   Leu   Val   Asn   Arg   Asp   Leu   Lys   Thr   Gln   Ser   Gly   Ser   Glu
                             275                        280                         285
     Met   Lys   Lys   Phe   Leu   Ser   Thr   Leu   Thr   Ile   Asp   Gly   Val   Thr   Arg   Ser
                             290                        295                         300
     Asp   Gln   Gly   Leu   Tyr   Thr   Cys   Ala   Ala   Ser   Ser   Gly   Leu   Met   Thr   Lys
     305                                 310                        315                         320
     Lys   Asn   Ser   Thr   Phe   Val   Arg   Val   His   Glu   Lys   Pro   Phe   Val   Ala   Phe
                             325                        330                         335
     Gly   Ser   Gly   Met   Glu   Ser   Leu   Val   Glu   Ala   Thr   Val   Gly   Glu   Arg   Val
                             340                        345                         350
     Arg   Ile   Pro   Ala   Lys   Tyr   Leu   Gly   Tyr   Pro   Pro   Pro   Glu   Ile   Lys   Trp
                             355                        360                         365
     Tyr   Lys   Asn   Gly   Ile   Pro   Leu   Glu   Ser   Asn   His   Thr   Ile   Lys   Ala   Gly
                             370                        375                         380
     His   Val   Leu   Thr   Ile   Met   Glu   Val   Ser   Glu   Arg   Asp   Thr   Gly   Asn   Tyr
     385                                 390                        395                         400
     Thr   Val   Ile   Leu   Thr   Asn   Pro   Ile   Ser   Lys   Glu   Lys   Gln   Ser   His   Val
                             405                        410                         415
     Val   Ser   Leu   Val   Val   Tyr   Val   Pro   Pro   Gln   Ile   Gly   Glu   Lys   Ser   Leu
                             420                        425                         430
     Ile   Ser   Pro   Val   Asp   Ser   Tyr   Gln   Tyr   Gly   Thr   Thr   Gln   Thr   Leu   Thr
                             435                        440                         445
     Cys   Thr   Val   Tyr   Ala   Ile   Pro   Pro   Pro   His   His   Ile   His   Trp   Tyr   Trp
                             450                        455                         460
     Gln   Leu   Glu   Glu   Glu   Cys   Ala   Asn   Glu   Pro   Ser   Gln   Ala   Val   Ser   Val
     465                                 470                        475                         480
     Thr   Asn   Pro   Tyr   Pro   Cys   Glu   Glu   Trp   Arg   Ser   Val   Glu   Asp   Phe   Gln
                             485                        490                         495
     Gly   Gly   Asn   Lys   Ile   Ala   Val   Asn   Lys   Asn   Gln   Phe   Ala   Leu   Ile   Glu
                             500                        505                         510
```

```
Gly  Lys  Asn  Lys  Thr  Val  Ser  Thr  Leu  Val  Ile  Gln  Ala  Ala  Asn  Val
          515                520                     525

Ser  Ala  Leu  Tyr  Lys  Cys  Glu  Ala  Val  Asn  Lys  Val  Gly  Arg  Gly  Glu
     530                535                     540

Arg  Val  Ile  Ser  Phe  His  Val  Thr  Arg  Gly  Pro  Glu  Ile  Thr  Leu  Gln
545                      550                     555                          560

Pro  Asp  Met  Gln  Pro  Thr  Glu  Gln  Glu  Ser  Val  Ser  Leu  Trp  Cys  Thr
                    565                          570                     575

Ala  Asp  Arg  Ser  Thr  Phe  Glu  Asn  Leu  Thr  Trp  Tyr  Lys  Leu  Gly  Pro
               580                     585                          590

Gln  Pro  Leu  Pro  Ile  His  Val  Gly  Glu  Leu  Pro  Thr  Pro  Val  Cys  Lys
          595                     600                          605

Asn  Leu  Asp  Thr  Leu  Trp  Lys  Leu  Asn  Ala  Thr  Met  Phe  Ser  Asn  Ser
     610                     615                     620

Thr  Asn  Asp  Ile  Leu  Ile  Met  Glu  Leu  Lys  Asn  Ala  Ser  Leu  Gln  Asp
625                          630                    635                          640

Gln  Gly  Asp  Tyr  Val  Cys  Leu  Ala  Gln  Asp  Arg  Lys  Thr  Lys  Lys  Arg
                    645                     650                          655

His  Cys  Val  Val  Arg  Gln  Leu  Thr  Val  Leu  Glu  Arg
               660                     665
```

( 2 ) INFORMATION FOR SEQ ID NO:14:

( i ) SEQUENCE CHARACTERISTICS:
        ( A ) LENGTH: 780 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:14:

```
Met  Val  Ser  Tyr  Trp  Asp  Thr  Gly  Val  Leu  Leu  Cys  Ala  Leu  Leu  Ser
 1                   5                         10                         15

Cys  Leu  Leu  Leu  Thr  Gly  Ser  Ser  Ser  Gly  Ser  Lys  Leu  Lys  Asp  Pro
               20                    25                          30

Glu  Leu  Ser  Leu  Lys  Gly  Thr  Gln  His  Ile  Met  Gln  Ala  Gly  Gln  Thr
          35                     40                          45

Leu  His  Leu  Gln  Cys  Arg  Gly  Glu  Ala  Ala  His  Lys  Trp  Ser  Leu  Pro
     50                     55                          60

Glu  Met  Val  Ser  Lys  Glu  Ser  Glu  Arg  Leu  Ser  Ile  Thr  Lys  Ser  Ala
65                        70                     75                           80

Cys  Gly  Arg  Asn  Gly  Lys  Gln  Phe  Cys  Ser  Thr  Leu  Thr  Leu  Asn  Thr
                    85                     90                          95

Ala  Gln  Ala  Asn  His  Thr  Gly  Phe  Tyr  Ser  Cys  Lys  Tyr  Leu  Ala  Val
                    100                    105                    110

Pro  Thr  Ser  Lys  Lys  Lys  Glu  Thr  Glu  Ser  Ala  Ile  Tyr  Ile  Phe  Ile
               115                    120                    125

Ser  Asp  Thr  Gly  Arg  Pro  Phe  Val  Glu  Met  Tyr  Ser  Glu  Ile  Pro  Glu
     130                    135                    140

Ile  Ile  His  Met  Thr  Glu  Gly  Arg  Glu  Leu  Val  Ile  Pro  Cys  Arg  Val
145                      150                    155                           160

Thr  Ser  Pro  Asn  Ile  Thr  Val  Thr  Leu  Lys  Lys  Phe  Pro  Leu  Asp  Thr
                    165                    170                         175

Leu  Ile  Pro  Asp  Gly  Lys  Arg  Ile  Ile  Trp  Asp  Ser  Arg  Lys  Gly  Phe
               180                    185                         190

Ile  Ile  Ser  Asn  Ala  Thr  Tyr  Lys  Glu  Ile  Gly  Leu  Leu  Thr  Cys  Glu
```

-continued

```
                    195                              200                              205
Ala  Thr  Val  Asn  Gly  His  Leu  Tyr  Lys  Thr  Asn  Tyr  Leu  Thr  His  Arg
     210                 215                      220

Gln  Thr  Asn  Thr  Ile  Ile  Asp  Val  Gln  Ile  Ser  Thr  Pro  Arg  Pro  Val
225                      230                 235                           240

Lys  Leu  Leu  Arg  Gly  His  Thr  Leu  Val  Leu  Asn  Cys  Thr  Ala  Thr  Thr
                    245                 250                           255

Pro  Leu  Asn  Thr  Arg  Val  Gln  Met  Thr  Trp  Ser  Tyr  Pro  Asp  Glu  Lys
                         260            265                 270

Asn  Lys  Arg  Ala  Ser  Val  Arg  Arg  Ile  Asp  Gln  Ser  Asn  Ser  His
          275                      280                 285

Ala  Asn  Ile  Phe  Tyr  Ser  Val  Leu  Thr  Ile  Asp  Lys  Met  Gln  Asn  Lys
     290                      295                      300

Asp  Lys  Gly  Leu  Tyr  Thr  Cys  Arg  Val  Arg  Ser  Gly  Pro  Ser  Phe  Lys
305                           310                 315                      320

Ser  Val  Asn  Thr  Ser  Val  His  Ile  Tyr  Asp  Lys  Ala  Phe  Ile  Thr  Val
               325                 330                           335

Lys  His  Arg  Lys  Gln  Gln  Val  Leu  Glu  Thr  Val  Ala  Gly  Lys  Arg  Ser
          340                      345                      350

Tyr  Arg  Leu  Ser  Met  Lys  Val  Lys  Ala  Phe  Pro  Ser  Pro  Glu  Val  Val
          355                      360                 365

Trp  Leu  Lys  Asp  Gly  Leu  Pro  Ala  Thr  Glu  Lys  Ser  Ala  Arg  Tyr  Leu
     370                      375                 380

Thr  Arg  Gly  Tyr  Ser  Leu  Ile  Ile  Lys  Asp  Val  Thr  Glu  Glu  Asp  Ala
385                      390                 395                           400

Gly  Asn  Tyr  Thr  Ile  Leu  Leu  Ser  Ile  Lys  Gln  Ser  Asn  Val  Phe  Lys
               405                      410                      415

Asn  Leu  Thr  Ala  Thr  Leu  Ile  Val  Asn  Val  Lys  Pro  Gln  Ile  Tyr  Glu
               420                      425                 430

Lys  Ala  Val  Ser  Ser  Phe  Pro  Asp  Pro  Ala  Leu  Tyr  Pro  Leu  Gly  Ser
          435                      440                 445

Arg  Gln  Ile  Leu  Thr  Cys  Thr  Ala  Tyr  Gly  Ile  Pro  Gln  Pro  Thr  Ile
     450                      455                 460

Lys  Trp  Phe  Trp  His  Pro  Cys  Asn  His  Asn  His  Ser  Glu  Ala  Arg  Cys
465                      470                 475                           480

Asp  Phe  Cys  Ser  Asn  Asn  Glu  Glu  Ser  Phe  Ile  Leu  Asp  Ala  Asp  Ser
               485                      490                      495

Asn  Met  Gly  Asn  Arg  Ile  Glu  Ser  Ile  Thr  Gln  Arg  Met  Ala  Ile  Ile
               500                 505                      510

Glu  Gly  Lys  Asn  Lys  Met  Ala  Ser  Thr  Leu  Val  Val  Ala  Asp  Ser  Arg
          515                      520                      525

Ile  Ser  Gly  Ile  Tyr  Ile  Cys  Ile  Ala  Ser  Asn  Lys  Val  Gly  Thr  Val
     530                      535                      540

Gly  Arg  Asn  Ile  Ser  Phe  Tyr  Ile  Thr  Asp  Val  Pro  Asn  Gly  Phe  His
545                      550                      555                      560

Val  Asn  Leu  Glu  Lys  Met  Pro  Thr  Glu  Gly  Glu  Asp  Leu  Lys  Leu  Ser
               565                      570                      575

Cys  Thr  Val  Asn  Lys  Phe  Leu  Tyr  Arg  Asp  Val  Thr  Trp  Ile  Leu  Leu
               580                      585                      590

Arg  Thr  Val  Asn  Asn  Arg  Thr  Met  His  Tyr  Ser  Ile  Ser  Lys  Gln  Lys
               595                 600                      605

Met  Ala  Ile  Thr  Lys  Glu  His  Ser  Ile  Thr  Leu  Asn  Leu  Thr  Ile  Met
610                      615                      620
```

```
Asn  Val  Ser  Leu  Gln  Asp  Ser  Gly  Thr  Tyr  Ala  Cys  Arg  Ala  Arg  Asn
625                      630                 635                          640

Val  Tyr  Thr  Gly  Glu  Glu  Ile  Leu  Gln  Lys  Lys  Glu  Ile  Thr  Ile  Arg
                         645                 650                          655

Asp  Gln  Glu  Ala  Pro  Tyr  Leu  Leu  Arg  Asn  Leu  Ser  Asp  His  Thr  Val
                    660                      665                 670

Ala  Ile  Ser  Ser  Ser  Thr  Thr  Leu  Asp  Cys  His  Ala  Asn  Gly  Val  Pro
               675                 680                      685

Glu  Pro  Gln  Ile  Thr  Trp  Phe  Lys  Asn  Asn  His  Lys  Ile  Gln  Gln  Glu
          690                      695                 700

Pro  Gly  Ile  Ile  Leu  Gly  Pro  Gly  Ser  Ser  Thr  Leu  Phe  Ile  Glu  Arg
705                      710                 715                          720

Val  Thr  Glu  Glu  Asp  Glu  Gly  Val  Tyr  His  Cys  Lys  Ala  Thr  Asn  Gln
                    725                      730                          735

Lys  Gly  Ser  Val  Glu  Ser  Ser  Ala  Tyr  Leu  Thr  Val  Gln  Gly  Thr  Ser
               740                      745                      750

Asp  Lys  Ser  Asn  Leu  Glu  Leu  Ile  Thr  Leu  Thr  Cys  Thr  Cys  Val  Ala
          755                      760                 765

Ala  Thr  Leu  Phe  Trp  Leu  Leu  Leu  Thr  Leu  Leu  Ile
     770                      775                 780
```

( 2 ) INFORMATION FOR SEQ ID NO:15:

( i ) SEQUENCE CHARACTERISTICS:
        ( A ) LENGTH: 788 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:15:

```
Met  Gln  Ser  Lys  Val  Leu  Leu  Ala  Val  Ala  Leu  Trp  Leu  Cys  Val  Glu
1                   5                   10                      15

Thr  Arg  Ala  Ala  Ser  Val  Gly  Leu  Pro  Ser  Val  Ser  Leu  Asp  Leu  Pro
               20                      25                      30

Arg  Leu  Ser  Ile  Gln  Lys  Asp  Ile  Leu  Thr  Ile  Lys  Ala  Asn  Thr  Thr
               35                      40                      45

Leu  Gln  Ile  Thr  Cys  Arg  Gly  Gln  Arg  Asp  Leu  Asp  Trp  Leu  Trp  Pro
     50                      55                      60

Asn  Asn  Gln  Ser  Gly  Ser  Glu  Gln  Arg  Val  Glu  Val  Thr  Glu  Cys  Ser
65                       70                      75                       80

Asp  Gly  Leu  Phe  Cys  Lys  Thr  Leu  Thr  Ile  Pro  Lys  Val  Ile  Gly  Asn
               85                      90                      95

Asp  Thr  Gly  Ala  Tyr  Lys  Cys  Phe  Tyr  Arg  Glu  Thr  Asp  Leu  Ala  Ser
               100                     105                     110

Val  Ile  Tyr  Val  Tyr  Val  Gln  Asp  Tyr  Arg  Ser  Pro  Phe  Ile  Ala  Ser
          115                     120                     125

Val  Ser  Asp  Gln  His  Gly  Val  Val  Tyr  Ile  Thr  Glu  Asn  Lys  Asn  Lys
     130                     135                     140

Thr  Val  Val  Ile  Pro  Cys  Leu  Gly  Ser  Ile  Ser  Asn  Leu  Asn  Val  Ser
145                     150                     155                      160

Leu  Cys  Ala  Arg  Tyr  Pro  Glu  Lys  Arg  Phe  Val  Pro  Asp  Gly  Asn  Arg
               165                     170                     175

Ile  Ser  Trp  Asp  Ser  Lys  Lys  Gly  Phe  Thr  Ile  Pro  Ser  Tyr  Met  Ile
               180                     185                     190

Ser  Tyr  Ala  Gly  Met  Val  Phe  Cys  Glu  Ala  Lys  Ile  Asn  Asp  Glu  Ser
```

-continued

|  |  |  | 195 |  |  | 200 |  |  |  |  | 205 |  |  |
|---|---|---|---|---|---|---|---|---|---|---|---|---|---|
| Tyr | Gln 210 | Ser | Ile | Met | Tyr 215 | Ile | Val | Val | Val | Gly 220 | Tyr | Arg | Ile | Tyr |
| Asp 225 | Val | Val | Leu | Ser | Pro 230 | Ser | His | Gly | Ile | Glu 235 | Leu | Ser | Val | Gly | Glu 240 |
| Lys | Leu | Val | Leu | Asn 245 | Cys | Thr | Ala | Arg | Thr 250 | Glu | Leu | Asn | Val | Gly 255 | Ile |
| Asp | Phe | Asn | Trp 260 | Glu | Tyr | Pro | Ser | Ser 265 | Lys | His | Gln | His | Lys 270 | Lys | Leu |
| Val | Asn | Arg 275 | Asp | Leu | Lys | Thr | Gln 280 | Ser | Gly | Ser | Glu | Met 285 | Lys | Lys | Phe |
| Leu | Ser 290 | Thr | Leu | Thr | Ile | Asp 295 | Gly | Val | Thr | Arg | Ser 300 | Asp | Gln | Gly | Leu |
| Tyr 305 | Thr | Cys | Ala | Ala | Ser 310 | Ser | Gly | Leu | Met | Thr 315 | Lys | Lys | Asn | Ser | Thr 320 |
| Phe | Val | Arg | Val | His 325 | Glu | Lys | Pro | Phe | Val 330 | Ala | Phe | Gly | Ser | Gly 335 | Met |
| Glu | Ser | Leu | Val 340 | Glu | Ala | Thr | Val | Gly 345 | Glu | Arg | Val | Arg | Ile 350 | Pro | Ala |
| Lys | Tyr | Leu 355 | Gly | Tyr | Pro | Pro | Pro 360 | Glu | Ile | Lys | Trp | Tyr 365 | Lys | Asn | Gly |
| Ile | Pro 370 | Leu | Glu | Ser | Asn | His 375 | Thr | Ile | Lys | Ala | Gly 380 | His | Val | Leu | Thr |
| Ile 385 | Met | Glu | Val | Ser | Glu 390 | Arg | Asp | Thr | Gly | Asn 395 | Tyr | Thr | Val | Ile | Leu 400 |
| Thr | Asn | Pro | Ile | Ser 405 | Lys | Glu | Lys | Gln | Ser 410 | His | Val | Val | Ser | Leu 415 | Val |
| Val | Tyr | Val | Pro 420 | Pro | Gln | Ile | Gly | Glu 425 | Lys | Ser | Leu | Ile | Ser 430 | Pro | Val |
| Asp | Ser | Tyr 435 | Gln | Tyr | Gly | Thr | Thr 440 | Gln | Thr | Leu | Thr | Cys 445 | Thr | Val | Tyr |
| Ala | Ile 450 | Pro | Pro | Pro | His | His 455 | Ile | His | Trp | Tyr | Trp 460 | Gln | Leu | Glu | Glu |
| Glu 465 | Cys | Ala | Asn | Glu | Pro 470 | Ser | Gln | Ala | Val | Ser 475 | Val | Thr | Asn | Pro | Tyr 480 |
| Pro | Cys | Glu | Glu | Trp 485 | Arg | Ser | Val | Glu | Asp 490 | Phe | Gln | Gly | Gly | Asn 495 | Lys |
| Ile | Ala | Val | Asn 500 | Lys | Asn | Gln | Phe | Ala 505 | Leu | Ile | Glu | Gly | Lys 510 | Asn | Lys |
| Thr | Val | Ser 515 | Thr | Leu | Val | Ile | Gln 520 | Ala | Ala | Asn | Val | Ser 525 | Ala | Leu | Tyr |
| Lys | Cys 530 | Glu | Ala | Val | Asn | Lys 535 | Val | Gly | Arg | Gly | Glu 540 | Arg | Val | Ile | Ser |
| Phe 545 | His | Val | Thr | Arg | Gly 550 | Pro | Glu | Ile | Thr | Leu 555 | Gln | Pro | Asp | Met | Gln 560 |
| Pro | Thr | Glu | Gln | Glu 565 | Ser | Val | Ser | Leu | Trp 570 | Cys | Thr | Ala | Asp | Arg 575 | Ser |
| Thr | Phe | Glu | Asn 580 | Leu | Thr | Trp | Tyr | Lys 585 | Leu | Gly | Pro | Gln | Pro 590 | Leu | Pro |
| Ile | His | Val 595 | Gly | Glu | Leu | Pro | Thr 600 | Pro | Val | Cys | Lys | Asn 605 | Leu | Asp | Thr |
| Leu | Trp 610 | Lys | Leu | Asn | Ala | Thr 615 | Met | Phe | Ser | Asn | Ser 620 | Thr | Asn | Asp | Ile |

| Leu | Ile | Met | Glu | Leu | Lys | Asn | Ala | Ser | Leu | Gln | Asp | Gln | Gly | Asp | Tyr |
| --- | --- | --- | --- | --- | --- | --- | --- | --- | --- | --- | --- | --- | --- | --- | --- |
| 625 | | | | 630 | | | | | 635 | | | | | | 640 |

| Val | Cys | Leu | Ala | Gln | Asp | Arg | Lys | Thr | Lys | Arg | His | Cys | Val | Val |
| --- | --- | --- | --- | --- | --- | --- | --- | --- | --- | --- | --- | --- | --- | --- |
| | | | | 645 | | | | | 650 | | | | | 655 |

| Arg | Gln | Leu | Thr | Val | Leu | Glu | Arg | Val | Ala | Pro | Thr | Ile | Thr | Gly | Asn |
| --- | --- | --- | --- | --- | --- | --- | --- | --- | --- | --- | --- | --- | --- | --- | --- |
| | | | 660 | | | | | 665 | | | | | 670 | | |

| Leu | Glu | Asn | Gln | Thr | Thr | Ser | Ile | Gly | Glu | Ser | Ile | Glu | Val | Ser | Cys |
| --- | --- | --- | --- | --- | --- | --- | --- | --- | --- | --- | --- | --- | --- | --- | --- |
| | | 675 | | | | | 680 | | | | | 685 | | | |

| Thr | Ala | Ser | Gly | Asn | Pro | Pro | Pro | Gln | Ile | Met | Trp | Phe | Lys | Asp | Asn |
| --- | --- | --- | --- | --- | --- | --- | --- | --- | --- | --- | --- | --- | --- | --- | --- |
| | | 690 | | | | 695 | | | | | 700 | | | | |

| Glu | Thr | Leu | Val | Glu | Asp | Ser | Gly | Ile | Val | Leu | Lys | Asp | Gly | Asn | Arg |
| --- | --- | --- | --- | --- | --- | --- | --- | --- | --- | --- | --- | --- | --- | --- | --- |
| 705 | | | | | 710 | | | | | 715 | | | | | 720 |

| Asn | Leu | Thr | Ile | Arg | Arg | Val | Arg | Lys | Glu | Asp | Glu | Gly | Leu | Tyr | Cys |
| --- | --- | --- | --- | --- | --- | --- | --- | --- | --- | --- | --- | --- | --- | --- | --- |
| | | | | 725 | | | | | 730 | | | | | 735 | |

| Gln | Ala | Cys | Ser | Val | Leu | Gly | Cys | Ala | Lys | Val | Glu | Ala | Phe | Phe | Ile |
| --- | --- | --- | --- | --- | --- | --- | --- | --- | --- | --- | --- | --- | --- | --- | --- |
| | | | 740 | | | | | 745 | | | | | 750 | | |

| Ile | Glu | Gly | Ala | Gln | Glu | Lys | Thr | Asn | Leu | Glu | Ile | Ile | Ile | Leu | Val |
| --- | --- | --- | --- | --- | --- | --- | --- | --- | --- | --- | --- | --- | --- | --- | --- |
| | | 755 | | | | | 760 | | | | | 765 | | | |

| Gly | Thr | Thr | Val | Ile | Ala | Met | Phe | Phe | Trp | Leu | Leu | Leu | Val | Ile | Ile |
| --- | --- | --- | --- | --- | --- | --- | --- | --- | --- | --- | --- | --- | --- | --- | --- |
| | 770 | | | | | 775 | | | | | 780 | | | | |

| Leu | Gly | Thr | Val |
| --- | --- | --- | --- |
| 785 | | | |

( 2 ) INFORMATION FOR SEQ ID NO:16:

( i ) SEQUENCE CHARACTERISTICS:
        ( A ) LENGTH: 2264 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:16:

```
GGTGTGGTCG CTGCGTTTCC TCTGCCTGCG CCGGGCATCA CTTGCGCGCC GCAGAAAGTC      60

CGTCTGGCAG CCTGGATATC CTCTCCTACC GGCACCCGCA GACGCCCTG  CAGCCGCGGT     120

CGGCGCCCGG GCTCCCTAGC CCTGTGCGCT CAACTGTCCT GCGCTGCGGG GTGCCGCGAG     180

TTCCACCTCC GCGCCTCCTT CTCTAGACAG GCGCTGGGAG AAAGAACCGG CTCCCGAGTT     240

CCGGCATTTC GCCCGGCTCG AGGTGCAGGA TGCAGAGCAA GGTGCTGCTG GCCGTCGCCC     300

TGTGGCTCTG CGTGGAGACC CGGGCCGCCT CTGTGGGTTT GCCTAGTGTT TCTCTTGATC     360

TGCCCAGGCT CAGCATACAA AAAGACATAC TTACAATTAA GGCTAATACA ACTCTTCAAA     420

TTACTTGCAG GGGACAGAGG GACTTGGACT GGCTTTGGCC CAATAATCAG AGTGGCAGTG     480

AGCAAAGGGT GGAGGTGACT GAGTGCAGCG ATGGCCTCTT CTGTAAGACA CTCACAATTC     540

CAAAAGTGAT CGGAAATGAC ACTGGAGCCT ACAAGTGCTT CTACCGGGAA ACTGACTTGG     600

CCTCGGTCAT TTATGTCTAT GTTCAAGATT ACAGATCTCC ATTTATTGCT TCTGTTAGTG     660

ACCAACATGG AGTCGTGTAC ATTACTGAGA ACAAAAACAA AACTGGTG   ATTCCATGTC     720

TCGGGTCCAT TTCAAATCTC AACGTGTCAC TTTGTGCAAG ATACCCAGAA AAGAGATTTG     780

TTCCTGATGG TAACAGAATT CCTGGGACA  GCAAGAAGGG CTTTACTATT CCCAGCTACA     840

TGATCAGCTA TGCTGGCATG GTCTTCTGTG AAGCAAAAAT TAATGATGAA AGTTACCAGT     900

CTATTATGTA CATAGTTGTC GTTGTAGGGT ATAGGATTTA TGATGTGGTT CTGAGTCCGT     960

CTCATGGAAT TGAACTATCT GTTGGAGAAA AGCTTGTCTT AAATTGTACA GCAAGAACTG    1020
```

-continued

```
AACTAAATGT GGGGATTGAC TTCAACTGGG AATACCCTTC TTCGAAGCAT CAGCATAAGA      1080
AACTTGTAAA CCGAGACCTA AAAACCCAGT CTGGGAGTGA GATGAAGAAA TTTTTGAGCA      1140
CCTTAACTAT AGATGGTGTA ACCCGGAGTG ACCAAGGATT GTACACCTGT GCAGCATCCA      1200
GTGGGCTGAT GACCAAGAAG AACAGCACAT TTGTCAGGGT CCATGAAAAA CCTTTTGTTG      1260
CTTTTGGAAG TGGCATGGAA TCTCTGGTGG AAGCCACGGT GGGGGAGCGT GTCAGAATCC      1320
CTGCGAAGTA CCTTGGTTAC CCACCCCCAG AAATAAAATG GTATAAAAAT GGAATACCCC      1380
TTGAGTCCAA TCACACAATT AAAGCGGGGC ATGTACTGAC GATTATGGAA GTGAGTGAAA      1440
GAGACACAGG AAATTACACT GTCATCCTTA CCAATCCCAT TTCAAAGGAG AAGCAGAGCC      1500
ATGTGGTCTC TCTGGTTGTG TATGTCCCAC CCCAGATTGG TGAGAAATCT CTAATCTCTC      1560
CTGTGGATTC CTACCAGTAC GGCACCACTC AAACGCTGAC ATGTACGGTC TATGCCATTC      1620
CTCCCCCGCA TCACATCCAC TGGTATTGGC AGTTGGAGGA AGAGTGCGCC AACGAGCCCA      1680
GCCAAGCTGT CTCAGTGACA AACCCATACC CTTGTGAAGA ATGGAGAAGT GTGGAGGACT      1740
TCCAGGGAGG AAATAAAATT GCCGTTAATA AAAATCAATT TGCTCTAATT GAAGGAAAAA      1800
ACAAAACTGT AAGTACCCTT GTTATCCAAG CGGCAAATGT GTCAGCTTTG TACAAATGTG      1860
AAGCGGTCAA CAAAGTCGGG AGAGGAGAGA GGGTGATCTC CTTCCACGTG ACCAGGGGTC      1920
CTGAAATTAC TTTGCAACCT GACATGCAGC CCACTGAGCA GGAGAGCGTG TCTTTGTGGT      1980
GCACTGCAGA CAGATCTACG TTTGAGAACC TCACATGGTA CAAGCTTGGC CCACAGCCTC      2040
TGCCAATCCA TGTGGGAGAG TTGCCCACAC CTGTTTGCAA GAACTTGGAT ACTCTTTGGA      2100
AATTGAATGC CACCATGTTC TCTAATAGCA CAAATGACAT TTTGATCATG GAGCTTAAGA      2160
ATGCATCCTT GCAGGACCAA GGAGACTATG TCTGCCTTGC TCAAGACAGG AAGACCAAGA      2220
AAAGACATTG CGTGGTCAGG CAGCTCACAG TCCTAGAGCG TTAA                      2264
```

( 2 ) INFORMATION FOR SEQ ID NO:17:

( i ) SEQUENCE CHARACTERISTICS:
        ( A ) LENGTH: 2352 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:17:

```
GCGCTCACCA TGGTCAGCTA CTGGACACC GGGGTCCTGC TGTGCGCGCT GCTCAGCTGT        60
CTGCTTCTCA CAGGATCTAG TTCAGGTTCA AAATTAAAAG ATCCTGAACT GAGTTTAAAA      120
GGCACCCAGC ACATCATGCA AGCAGGCCAG ACACTGCATC TCCAATGCAG GGGGGAAGCA      180
GCCCATAAAT GGTCTTTGCC TGAAATGGTG AGTAAGGAAA GCGAAAGGCT GAGCATAACT      240
AAATCTGCCT GTGGAAGAAA TGGCAAACAA TTCTGCAGTA CTTTAACCTT GAACACAGCT      300
CAAGCAAACC ACACTGGCTT CTACAGCTGC AAATATCTAG CTGTACCTAC TTCAAAGAAG      360
AAGGAAACAG AATCTGCAAT CTATATATTT ATTAGTGATA CAGGTAGACC TTTCGTAGAG      420
ATGTACAGTG AAATCCCCGA AATTATACAC ATGACTGAAG GAAGGGAGCT CGTCATTCCC      480
TGCCGGGTTA CGTCACCTAA CATCACTGTT ACTTTAAAAA AGTTTCCACT TGACACTTTG      540
ATCCCTGATG GAAAACGCAT AATCTGGGAC AGTAGAAAGG GCTTCATCAT ATCAAATGCA      600
ACGTACAAAG AAATAGGGCT TCTGACCTGT GAAGCAACAG TCAATGGGCA TTTGTATAAG      660
ACAAACTATC TCACACATCG ACAAACCAAT ACAATCATAG ATGTCCAAAT AAGCACACCA      720
CGCCCAGTCA AATTACTTAG AGGCCATACT CTTGTCCTCA ATTGTACTGC TACCACTCCC      780
```

| | | | | | | |
|---|---|---|---|---|---|---|
|TTGAACACGA|GAGTTCAAAT|GACCTGGAGT|TACCCTGATG|AAAAAAATAA|GAGAGCTTCC|840|
|GTAAGGCGAC|GAATTGACCA|AAGCAATTCC|CATGCCAACA|TATTCTACAG|TGTTCTTACT|900|
|ATTGACAAAA|TGCAGAACAA|AGACAAGGA|CTTTATACTT|GTCGTGTAAG|GAGTGGACCA|960|
|TCATTCAAAT|CTGTTAACAC|CTCAGTGCAT|ATATATGATA|AAGCATTCAT|CACTGTGAAA|1020|
|CATCGAAAAC|AGCAGGTGCT|TGAAACCGTA|GCTGGCAAGC|GGTCTTACCG|GCTCTCTATG|1080|
|AAAGTGAAGG|CATTTCCCTC|GCCGGAAGTT|GTATGGTTAA|AAGATGGGTT|ACCTGCGACT|1140|
|GAGAAATCTG|CTCGCTATTT|GACTCGTGGC|TACTCGTTAA|TTATCAAGGA|CGTAACTGAA|1200|
|GAGGATGCAG|GGAATTATAC|AATCTTGCTG|AGCATAAAAC|AGTCAAATGT|GTTTAAAAAC|1260|
|CTCACTGCCA|CTCTAATTGT|CAATGTGAAA|CCCCAGATTT|ACGAAAGGC|CGTGTCATCG|1320|
|TTTCCAGACC|CGGCTCTCTA|CCCACTGGGC|AGCAGACAAA|TCCTGACTTG|TACCGCATAT|1380|
|GGTATCCCTC|AACCTACAAT|CAAGTGGTTC|TGGCACCCCT|GTAACCATAA|TCATTCCGAA|1440|
|GCAAGGTGTG|ACTTTTGTTC|CAATAATGAA|GAGTCCTTTA|TCCTGGATGC|TGACAGCAAC|1500|
|ATGGGAAACA|GAATTGAGAG|CATCACTCAG|CGCATGGCAA|TAATAGAAGG|AAAGAATAAG|1560|
|ATGGCTAGCA|CCTTGGTTGT|GGCTGACTCT|AGAATTTCTG|GAATCTACAT|TTGCATAGCT|1620|
|TCCAATAAAG|TTGGGACTGT|GGGAAGAAAC|ATAAGCTTTT|ATATCACAGA|TGTGCCAAAT|1680|
|GGGTTTCATG|TTAACTTGGA|AAAAATGCCG|ACGGAAGGAG|AGGACCTGAA|ACTGTCTTGC|1740|
|ACAGTAACA|AGTTCTTATA|CAGAGACGTT|ACTTGGATTT|TACTGCGGAC|AGTTAATAAC|1800|
|AGAACAATGC|ACTACAGTAT|TAGCAAGCAA|AAAATGGCCA|TCACTAAGGA|GCACTCCATC|1860|
|ACTCTTAATC|TTACCATCAT|GAATGTTTCC|CTGCAAGATT|CAGGCACCTA|TGCCTGCAGA|1920|
|GCCAGGAATG|TATACACAGG|GGAAGAAATC|CTCCAGAAGA|AAGAAATTAC|AATCAGAGAT|1980|
|CAGGAAGCAC|CATACCTCCT|GCGAAACCTC|AGTGATCACA|CAGTGGCCAT|CAGCAGTTCC|2040|
|ACCACTTTAG|ACTGTCATGC|TAATGGTGTC|CCCGAGCCTC|AGATCACTTG|GTTTAAAAAC|2100|
|AACCACAAAA|TACAACAAGA|GCCTGGAATT|ATTTTAGGAC|CAGGAAGCAG|CACGCTGTTT|2160|
|ATTGAAAGAG|TCACAGAAGA|GGATGAAGGT|GTCTATCACT|GCAAAGCCAC|CAACCAGAAG|2220|
|GGCTCTGTGG|AAAGTTCAGC|ATACCTCACT|GTTCAAGGAA|CCTCGGACAA|GTCTAATCTG|2280|
|GAGCTGATCA|CTCTAACATG|CACCTGTGTG|GCTGCGACTC|TCTTCTGGCT|CCTATTAACC|2340|
|CTCCTTATCT|AA| | | | |2352|

(2) INFORMATION FOR SEQ ID NO:18:

(i) SEQUENCE CHARACTERISTICS:
        (A) LENGTH: 2383 base pairs
        (B) TYPE: nucleic acid
        (C) STRANDEDNESS: single
        (D) TOPOLOGY: linear (ii) MOLECULE TYPE: Genomic DNA (xi) SEQUENCE DESCRIPTION: SEQ ID NO:18:

| | | | | | | |
|---|---|---|---|---|---|---|
|CTCGAGGTGC|AGGATGCAGA|GCAAGGTGCT|GCTGGCCGTC|GCCCTGTGGC|TCTGCGTGGA|60|
|GACCCGGGCC|GCCTCTGTGG|GTTTGCCTAG|TGTTTCTCTT|GATCTGCCCA|GGCTCAGCAT|120|
|ACAAAAAGAC|ATACTTACAA|TTAAGGCTAA|TACAACTCTT|CAAATTACTT|GCAGGGACA|180|
|GAGGGACTTG|GACTGGCTTT|GGCCCAATAA|TCAGAGTGGC|AGTGAGCAAA|GGGTGGAGGT|240|
|GACTGAGTGC|AGCGATGGCC|TCTTCTGTAA|GACACTCACA|ATTCCAAAAG|TGATCGGAAA|300|
|TGACACTGGA|GCCTACAAGT|GCTTCTACCG|GGAAACTGAC|TTGGCCTCGG|TCATTTATGT|360|

```
CTATGTTCAA  GATTACAGAT  CTCCATTTAT  TGCTTCTGTT  AGTGACCAAC  ATGGAGTCGT      420
GTACATTACT  GAGAACAAAA  ACAAAACTGT  GGTGATTCCA  TGTCTCGGGT  CCATTTCAAA      480
TCTCAACGTG  TCACTTTGTG  CAAGATACCC  AGAAAAGAGA  TTTGTTCCTG  ATGGTAACAG      540
AATTTCCTGG  GACAGCAAGA  AGGGCTTTAC  TATTCCCAGC  TACATGATCA  GCTATGCTGG      600
CATGGTCTTC  TGTGAAGCAA  AAATTAATGA  TGAAAGTTAC  CAGTCTATTA  TGTACATAGT      660
TGTCGTTGTA  GGGTATAGGA  TTTATGATGT  GGTTCTGAGT  CCGTCTCATG  GAATTGAACT      720
ATCTGTTGGA  GAAAAGCTTG  TCTTAAATTG  TACAGCAAGA  ACTGAACTAA  ATGTGGGGAT      780
TGACTTCAAC  TGGGAATACC  CTTCTTCGAA  GCATCAGCAT  AAGAAACTTG  TAAACCGAGA      840
CCTAAAAACC  CAGTCTGGGA  GTGAGATGAA  GAAATTTTTG  AGCACCTTAA  CTATAGATGG      900
TGTAACCCGG  AGTGACCAAG  GATTGTACAC  CTGTGCAGCA  TCCAGTGGGC  TGATGACCAA      960
GAAGAACAGC  ACATTTGTCA  GGGTCCATGA  AAAACCTTTT  GTTGCTTTTG  GAAGTGGCAT     1020
GGAATCTCTG  GTGGAAGCCA  CGGTGGGGGA  GCGTGTCAGA  ATCCCTGCGA  AGTACCTTGG     1080
TTACCCACCC  CCAGAAATAA  AATGGTATAA  AAATGGAATA  CCCCTTGAGT  CCAATCACAC     1140
AATTAAAGCG  GGGCATGTAC  TGACGATTAT  GGAAGTGAGT  GAAAGAGACA  CAGGAAATTA     1200
CACTGTCATC  CTTACCAATC  CCATTTCAAA  GGAGAAGCAG  AGCCATGTGG  TCTCTCTGGT     1260
TGTGTATGTC  CCACCCCAGA  TTGGTGAGAA  ATCTCTAATC  TCTCCTGTGG  ATTCCTACCA     1320
GTACGGCACC  ACTCAAACGC  TGACATGTAC  GGTCTATGCC  ATTCCTCCCC  CGCATCACAT     1380
CCACTGGTAT  TGGCAGTTGG  AGGAAGAGTG  CGCCAACGAG  CCCAGCCAAG  CTGTCTCAGT     1440
GACAAACCCA  TACCCTTGTG  AAGAATGGAG  AAGTGTGGAG  GACTTCCAGG  GAGGAAATAA     1500
AATTGCCGTT  AATAAAAATC  AATTTGCTCT  AATTGAAGGA  AAAACAAAA   CTGTAAGTAC     1560
CCTTGTTATC  CAAGCGGCAA  ATGTGTCAGC  TTTGTACAAA  TGTGAAGCGG  TCAACAAAGT     1620
CGGGAGAGGA  GAGAGGGTGA  TCTCCTTCCA  CGTGACCAGG  GGTCCTGAAA  TTACTTTGCA     1680
ACCTGACATG  CAGCCCACTG  AGCAGGAGAG  CGTGTCTTTG  TGGTGCACTG  CAGACAGATC     1740
TACGTTTGAG  AACCTCACAT  GGTACAAGCT  TGGCCCACAG  CCTCTGCCAA  TCCATGTGGG     1800
AGAGTTGCCC  ACACCTGTTT  GCAAGAACTT  GGATACTCTT  TGGAAATTGA  ATGCCACCAT     1860
GTTCTCTAAT  AGCACAAATG  ACATTTGAT   CATGGAGCTT  AAGAATGCAT  CCTTGCAGGA     1920
CCAAGGAGAC  TATGTCTGCC  TTGCTCAAGA  CAGGAAGACC  AAGAAAAGAC  ATTGCGTGGT     1980
CAGGCAGCTC  ACAGTCCTAG  AGCGTGTGGC  ACCCACGATC  ACAGGAAACC  TGGAGAATCA     2040
GACGACAAGT  ATTGGGGAAA  GCATCGAAGT  CTCATGCACG  GCATCTGGGA  ATCCCCCTCC     2100
ACAGATCATG  TGGTTTAAAG  ATAATGAGAC  CCTTGTAGAA  GACTCAGGCA  TTGTATTGAA     2160
GGATGGGAAC  CGGAACCTCA  CTATCCGCAG  AGTGAGGAAG  GAGGACGAAG  GCCTCTACAC     2220
CTGCCAGGCA  TGCAGTGTTC  TTGGCTGTGC  AAAAGTGGAG  GCATTTTTCA  TAATAGAAGG     2280
TGCCCAGGAA  AAGACGAACT  TGGAAATCAT  TATTCTAGTA  GGCACGACGG  TGATTGCCAT     2340
GTTCTTCTGG  CTACTTCTTG  TCATCATCCT  AGGGACCGTT  TAA                        2383
```

INHIBITOR OF VASCULAR ENDOTHELIAL CELL GROWTH FACTOR

RELATED APPLICATIONS

This is a division of Ser. No. 08/232,538 filed Apr. 21, 1994 and a continuation-in-part application of application Ser. No. 08/038,769 filed Mar. 25, 1993.

BACKGROUND OF THE DISCLOSURE

Recently a new class of cell-derived dimeric mitogens with selectivity for vascular endothelial cells has been identified and designated vascular endothelial cell growth factor (VEGF). VEGF has been purified from conditioned growth media of rat glioma cells [Conn et al., (1990), Proc. Natl. Acad. Sci. U.S.A., 87, pp 2628–2632]; and conditioned growth media of bovine pituitary folliculo stellate cells [Ferrara and Henzel, (1989), Biochem. Biophys. Res. Comm., 161, pp. 851–858; Gozpadorowicz et al., (1989), Proc. Natl. Acad. Sci. U.S.A., 86, pp. 7311–7315] and conditioned growth medium from human U937 cells [Connolly, D. T. et al. (1989), Science, 246, pp. 1309–1312]. VEGF is a dimer with an apparent molecular mass of about 46 kDa with each subunit having an apparent molecular mass of about 23 kDa. VEGF has some structural similarities to platelet derived growth factor (PDGF), which is a mitogen for connective tissue cells but not mitogenic for vascular endothelial cells from large vessels.

The membrane-bound tyrosine kinase receptor, known as FLT, was shown to be a VEGF receptor [DeVries, C. et al., (1992), Science, 255, pp.989–991]. The FLT receptor specifically binds VEGF which induces mitogenesis. Another form of the VEGF receptor, designated KDR, is also known to bind VEGF and induce mitogenesis. The partial cDNA sequence and nearly full length protein sequence of KDR is known as well [Terman, B. I. et al., (1991) Oncogene 6, pp. 1677–1683; Terman, B. I. et al., (1992) Biochem. Biophys. Res. Comm. 187, pp. 1579–1586].

Persistent angiogenesis may cause or exacerbate certain diseases such as psoriasis, rheumatoid arthritis, hemangiomas, angiofibromas, diabetic retinopathy and neovascular glaucoma. An inhibitor of VEGF activity would be useful as a treatment for such diseases and other VEGF-induced pathological angiogenesis and vascular permeability conditions, such as tumor vascularization.

SUMMARY OF THE DISCLOSURE

A naturally-occurring FLT messenger RNA (mRNA) was identified and cloned from vascular endothelial cells. This MRNA is shown to encode most of the extracellular, or soluble, portion of the VEGF receptor, FLT. Soluble receptor molecules including forms containing a C-terminal transmembrane region are also recombinantly engineered for this and other VEGF receptors. These soluble receptors, comprising truncated and modified forms are expressed in recombinant host cells and have VEGF binding properties. The soluble receptor proteins are useful as inhibitors of VEGF activity since they will bind available VEGF preventing it from activating its functional receptors on vascular endothelial cells and could form non-functional heterodimers with full-length membrane anchored VEGF receptors.

BRIEF DESCRIPTION OF THE DRAWINGS

FIGS. 2A–2B—The DNA sequence of the sVEGF-RI soluble VEGF receptor/VEGF inhibitor is shown.

FIG. 3—The amino acid sequence of the sVEGF-RI soluble VEGF receptor/VEGF inhibitor is shown.

FIGS. 10A–10B—The nucleotide sequence encoding sVEGF-RII is shown.

FIGS. 11A–11C—The amino acid sequence for sVEGF-RII is shown.

FIGS. 12A–12B—The nucleotide sequence encoding VEGF-RTMII is shown.

FIG. 13—The amino acid sequence for VEGF-RTMII is shown.

FIGS. 14A–14B—The nucleotide sequence encoding sVEGF-RTMI is shown.

FIG. 15—The amino acid sequence for sVEGF-RTMI is shown.

DETAILED DESCRIPTION OF THE DISCLOSURE

The present invention relates to cDNA encoding a soluble VEGF receptor protein (sVEGF-R) which is isolated from VEGF receptor producing cells or is recombinantly engineered from VEGF receptor-encoding DNA. sVEGF-R, as used herein, refers to a protein which can specifically bind to a vascular endothelial cell growth factor without stimulating mitogenesis of vascular endothelial cells.

The amino acid sequence of FLT is known, [Shibuya, M. et al., (1990), Oncogene, 5, pp.519–524] and corresponds to the full length cell-associated VEGF tyrosine kinase receptor. Other VEGF receptors are known to exist. Other known VEGF receptors include, but are not limited to KDR [Terman (1991), supra., and Terman (1992), supra.]. Mammalian cells capable of producing FLT, KDR and other VEGF receptors include, but are not limited to, vascular endothelial cells. Mammalian cell lines which produce FLT or KDR and other VEGF receptors include, but are not limited to, human endothelial cells. The preferred cells for the present invention include human umbilical vein endothelial cells (HUVEC).

Other cells and cell lines may also be suitable for use to isolate sVEGF-R cDNA. Selection of suitable cells may be done by screening for sVEGF-R binding activity on cell surfaces, in cell extracts or conditioned medium or by screening for gene expression by PCR or hybridization. Methods for detecting soluble receptor activity are well known in the art [Duan, D-S. R. et al., (1991) J.Biol.Chem., 266, pp.413–418] and measure the binding of labelled VEGF. Cells which possess VEGF binding activity in this assay may be suitable for the isolation of sVEGF-R cDNA.

Figure 1:
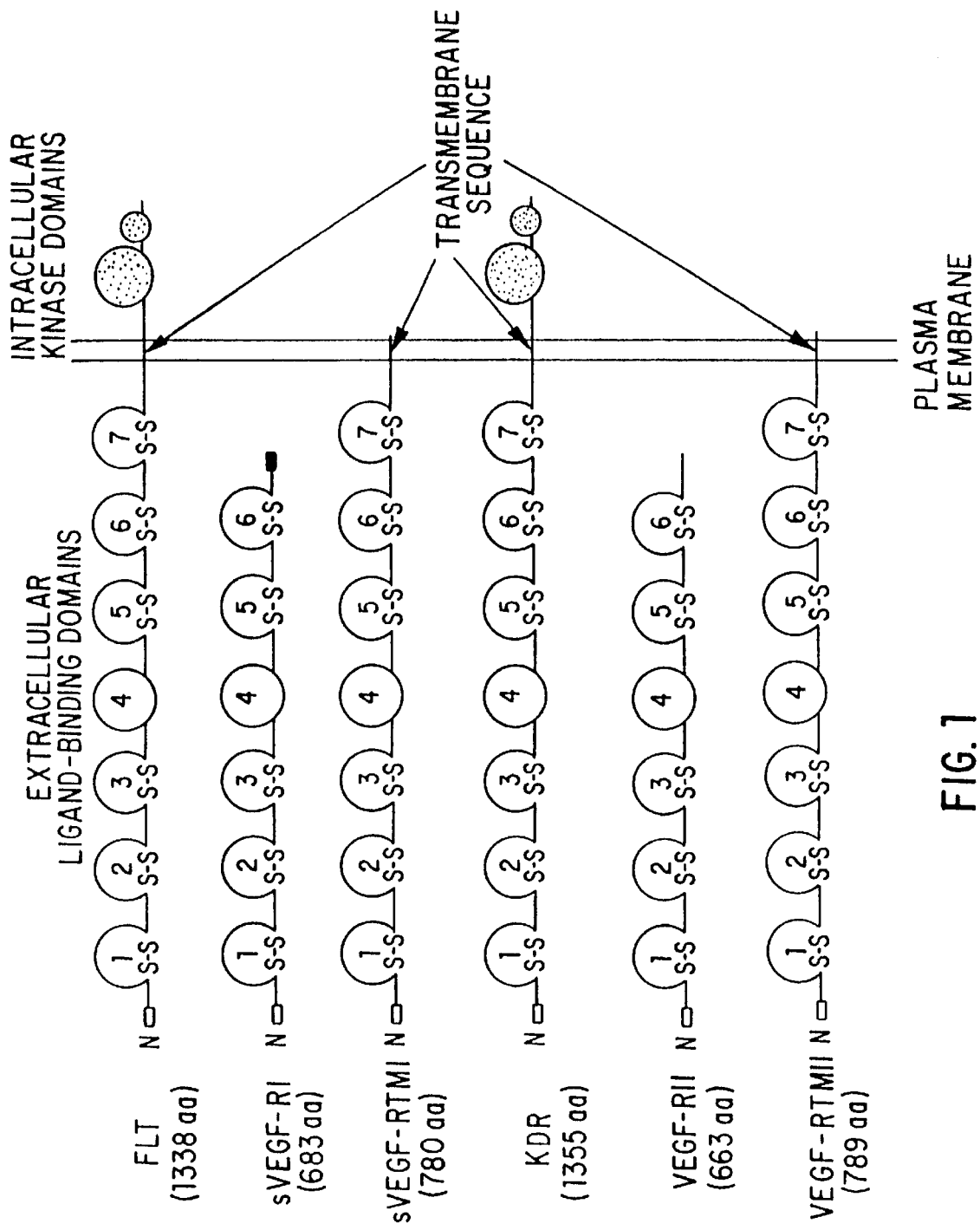
FIG. 1—A schematic diagram of full length VEGF receptors (FLT and KDR), the soluble VEGF receptors (sVEGF-RI and sVEGF-RII) and the soluble receptors containing the C-terminal transmembrane region (VEGF-RTMI and VEGF-RTMII) are shown with the protein domains of each.

Full length FLT producing cells such as human HUVEC cells (American Type Culture Collection, ATCC CRL 1730) [Hoshi, H. and McKeehan, W. L., Proc. Natl. Acad. Sci. U.S.A., (1984) 81, pp. 6413–6417] are grown according to the recommended culture conditions of the ATCC. Full length FLT, and KDR VEGF receptors as well as extracellular region (sVEGF-RI and sVEGF-RII) and extracellular region plus transmembrane region forms (sVEGF-RTMI and sVEGF-RTMII) are shown in FIG. 1. The full length receptor has an extracellular ligand binding region composed of about seven immunoglobulin-like domains, a membrane spanning sequence (transmembrane domain) and intracellular tyrosine kinase domains. The inhibitory forms of this receptor, which are the subject of the present invention, are also shown in FIG. 1 and lack the intracellular kinase domains, and for some inhibitors, the transmembrane sequence and the C-terminal most Ig-like extracellular domain.

Any of a variety of procedures may be used to molecularly clone sVEGF-R cDNA. These methods include, but are not limited to, direct functional expression of the sVEGF-R gene following the construction of an sVEGF-R-containing cDNA library in an appropriate expression vector system.

Another method is to screen a sVEGF-R-containing cDNA library constructed in a bacteriophage or plasmid shuttle vector with a labelled oligonucleotide probe designed from the predicted amino acid sequence of sVEGF-R. The preferred method consists of screening a sVEGF-R-containing cDNA library constructed in a bacteriophage or plasmid shuttle vector with a partial cDNA encoding at least part of the full length FLT protein. This partial cDNA is obtained by the specific PCR amplification of sVEGF-R DNA fragments through the design of oligonucleotide primers from the known sequence of the full length FLT-encoding DNA.

It is readily apparent to those skilled in the art that other types of libraries, as well as libraries constructed from other cells or cell types, may be useful for isolating sVEGF-R-encoding DNA. Other types of libraries include, but are not limited to, cDNA libraries derived from other cells or cell lines other than HUVECs and genomic DNA libraries.

It is readily apparent to those skilled in the art that suitable cDNA libraries may be prepared from cells or cell lines which have sVEGF-R activity. The selection of cells or cell lines for use in preparing a cDNA library to isolate sVEGF-R cDNA may be done by first measuring secreted sVEGF-R activity using the VEGF binding assay described fully herein.

Preparation of cDNA libraries can be performed by standard techniques well known in the art. Well known cDNA library construction techniques can be found for example, in Maniatis, T., Fritsch, E. F., Sambrook, J., Molecular Cloning: A Laboratory Manual (Cold Spring Harbor Laboratory, Cold Spring Harbor, New York, 1982).

It is also readily apparent to those skilled in the art that DNA encoding sVEGF-R may also be isolated from a suitable genomic DNA library. Construction of genomic DNA libraries can be performed by standard techniques well known in the art. Well known genomic DNA library construction techiques can be found in Maniatis, T., Fritsch, E. F., Sambrook, J. in Molecular Cloning: A Laboratory Manuel (Cold Spring Harbor Laboratory, Cold Spring Harbor, New York, 1982).

Another means of obtaining sVEGF-R molecules is to recombinantly engineer them from DNA encoding the partial or complete amino acid sequence of a VEGF receptor. Examples of other VEGF receptors include, but are not limited to, KDR. Using recombinant DNA techniques, DNA molecules are constructed which encode at least a portion of the VEGF receptor capable of binding VEGF without stimulating mitogenesis. Standard recombinant DNA techniques are used such as those found in Maniatis, et al., supra.

Using one of the preferred methods of the present invention, cDNA clones encoding sVEGF-R are isolated in a two-stage approach employing polymerase chain reaction (PCR) based technology and cDNA library screening. In the first stage, DNA oligonucleotides derived from the extracellular domain sequence information from the known full length FLT, KDR or other VEGF receptor is used to design degenerate oligonucleotide primers for the amplification of sVEGF-R-specific DNA fragments. In the second stage, these fragments are cloned to serve as probes for the isolation of complete sVEGF-R cDNA from a commercially available lambda gt10 cDNA library (Clontech) derived from HUVEC cells (ATCC CRL 1730).

These PCR derived products were used as hybridization probes for screening a lambda gt10 cDNA library derived from HUVECs (Clontech). Plating and plaque lifts of the library were performed by standard methods (T. Maniatis, E. F. Fritsch, J. Sambrook, Molecular Cloning: A Laboratory Manual (Cold Spring Harbor Laboratory, Cold Spring Harbor, New York, 1982). The probes were random-primed labelled with $^{32}$P-dCTP to high specific activity and a separate screening of the library ($1\times10^6$ plaques per screen) was conducted with each probe. The probes were added to hybridization buffer (50% formamide, 5X Denhardts, 6X SSC (1X SSC=0.15M NaCl, 0.015M Na3citrate-$2H_2O$, pH 7.0), 0.1% SDS, 100 mg/ml salmon sperm DNA) at $1\times10^6$ cpm/ml.

Four positively hybridizing phage were detected using the flt-specific probe. These positively hybridizing phage were observed to be less than full length flt.

Two flt cDNA clones of about 2.0 kb and 2.7 kb in length were subcloned into pGEM vectors (Promega) and bi-directionally sequenced in their entirety by the chain termination method (Sanger et al., (1977) P.N.A.S. USA, 74, pp. 5463–5467,) and shown to contain a single open reading frame of about 569 amino acids. Sequence analysis demonstrated that a portion of the 5' flt coding region was missing from these clones. The remainder of the 5' end was cloned using PCR and combined with the DNA of the clones lacking the 5' end to yield a single open reading frame encoding about 687 amino acids.

The sequence for the cDNA encoding flt-derived sVEGF-RI is shown in Table 1, and was identified in clones 7 and 11. The deduced amino acid sequence of sVEGF-RI from the cloned cDNA is shown in Table 2. Inspection of the deduced amino acid sequence reveals the presence of a single, large open reading frame of 687 amino acids. By comparison with amino acid sequence of the full length FLT VEGF receptor, 31 amino acids are encoded at the C-terminal end of the cDNA which are different from those of FLT.

Using another of the preferred methods of the present invention, DNA encoding sVEGF-R is constructed from a DNA sequence encoding a VEGF receptor. For purposes of illustration, DNA encoding the VEGF receptor known as KDR was utilized. Using the receptor DNA sequence, a DNA molecule is constructed which encodes the extracellular domain of the receptor, or the VEGF binding domain only and is denoted sVEGF-RII. Restriction endonuclease cleavage sites are identified within the receptor DNA and can be utilized directly to excise the extracellular-encoding portion. In addition, PCR techniques as described above may be utilized to produce the desired portion of DNA. It is readily apparent to those skilled in the art that other techniques, which are standard in the art, may be utilized to produce sVEGF-R molecules in a manner analagous to those described above. Such techniques are found, for example, in Maniatis et al., supra.

Additional truncated forms of the VEGF receptor are constructed which contain the transmembrane region. Retention of the transmembrane may facilitate orientation of the inhibitor molecule at the target cell surface. Examples of transmembrane region containing inhibitor molecules include but are not limited to those shown in FIG. 1. VEGF-RTMI and VEGF-RTMII, as shown in FIG. 1, are FLT-related and KDR-related, respectively, transmembrane region containing receptor inhibitors. Construction of transmembrane region containing molecules, such as VEGF-RTMI and VEGF-RTMII, is done by standard techniques known in the art including but not limited to utilizing convenient restriction endonuclease cleavage sites or PCR techniques as described herein. It is readily understood by those skilled in the art that various forms of the inhibitors of a VEGF receptor, as disclosed herein, containing only the extracellular region or containing, in addition, the transmembrane region may be constructed which have substantially the same activity.

The cloned sVEGF-R cDNA obtained through the methods described above may be recombinantly expressed by molecular cloning into an expression vector containing a suitable promoter and other appropriate transcription regulatory elements, and transferred into prokaryotic or eukaryotic host cells to produce recombinant sVEGF-R. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, fingal cells, yeast cells, plant cells, insect cells and animal cells.

Specifically designed vectors allow the shuttling of DNA between hosts such as bacteria-yeast or bacteria-animal or bacteria-insect cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant sVEGF-R in mammalian cells. Commercially available mammalian expression vectors which may be suitable for recombinant sVEGF-R expression, include but are not limited to, pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and gZD35 (ATCC 37565).

DNA encoding sVEGF-R may also be cloned into an expression vector for expression in a recombinant host cell. Recombinant host cells may be prokaryotic or eukaryotic, including but not limited to bacteria, yeast, mammalian cells including but not limited to cell lines of human, bovine, porcine, monkey and rodent origin, and insect cells including but not limited to drosophila, moth, mosquito and armyworm derived cell lines. Cell lines derived from mammalian species which may be suitable and which are commercially available, include but are not limited to, CV-1 (ATCC CCL 70), COS-1 (ATCC CRL 1650), COS-7 (ATCC CRL 1651), CHO-KL (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26) and MRC-5 (ATCC CCL 171). Insect cell lines which may be suitable and are commercially available include but are not limited to 3M-S (ATCC CRL 8851) moth (ATCC CCL 80) mosquito (ATCC CCL 194 and 195; ATCC CRL 1660 and 1591) and armyworm (Sf9, ATCC CRL 1711).

The expression vector may be introduced into host cells via any one of a number of techniques including but not limited to transformation, transfection, liposome or protoplast fusion, and electroporation. The expression vector-containing cells are clonally propagated and individually analyzed to determine whether they produce sVEGF-R protein. Identification of sVEGF-R expressing host cell clones may be done by several means, including but not limited to immunological reactivity with anti-sVEGF-R antibodies, binding to radiolabelled VEGF, and the presence of host cell-secreted sVEGF-R activity.

Expression of sVEGF-R DNA may also be performed using in vitro produced synthetic MRNA. Synthetic MRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

Levels of sVEGF-R protein produced by host cells may be quantitated by immunoaffinity and/or ligand affinity techniques. sVEGF-R-specific affinity beads or sVEGF-R-specific antibodies are used to isolate $^{35}$S-methionine labelled or unlabelled sVEGF-R protein. Labelled sVEGF-R protein is analyzed by SDS-PAGE. Unlabelled sVEGF-R protein is detected by Western blotting, ELISA or RIA assays employing sVEGF-R specific antibodies, or by ligand blotting with labelled VEGF.

Following expression of sVEGF-R in a recombinant host cell, sVEGF-R protein may be recovered to provide sVEGF-R in active form, capable of binding VEGF without stimulating mitogenesis. Several sVEGF-R purification procedures are available and suitable for use. sVEGF-R may be purified from cell lysates and extracts, or from conditioned culture medium, by various combinations of, or individual application of salt fractionation, ion exchange chromatography, size exclusion chromatography, hydroxylapatite adsorption chromatography, reversed phase chromatography, heparin sepharose chromatography, VEGF ligand affinity chromatography, and hydrophobic interaction chromatography.

In addition, recombinant sVEGF-R can be separated from other cellular proteins by use of an immuno-affinity column made with monoclonal or polyclonal antibodies specific for full length sVEGF-R, or polypeptide fragments of sVEGF-R.

Identification of sVEGF-RI—In an attempt to clone the VEGF receptor cDNA (flt) a HUVEC 1gt10 cDNA library was screened with a DNA probe derived from the extracellular domain of the membrane bound or full length form of this receptor as shown in FIG. 1. Four incomplete clones, all lacking various lengths of 5' coding sequence, were isolated from screening a total of $1 \times 10^6$ plaques. Two of these isolates represent partial clones that were identical to full length flt, one of which contained the complete 3' coding region of the form described by Shibuya et al., supra. The other two clones were identical to full length flt up to base pair number 2219 (Table 1 and FIGS. 2A–2B) where they then diverged from full length flt. These clones (clone 7 and 11) coded for an additional unique 31 amino acids before the open reading frame is terminated by a TAA codon (Table 2 and FIG. 3).

Clone 7 and 11 coded for a protein with a predicted molecular mass of about 75 kDa containing 12 putative N-linked glycosylation sites. This version of the receptor was missing the transmembrane and intracellular kinase domains and thus coded for a natural soluble form of the VEGF receptor (sVEGF-RI). Further, the protein molecule predicted by sVEGF-RI has only the first six Ig-like domains, missing the one closest to the transmembrane sequence (FIG. 1). The 31 amino acids at the C-terminal end of sVEGF-RI contain two cysteine residues, but does not resemble an Ig domain.

Expression of sVEGF-RI in Sf9 cells—To analyze the binding and biological properties of this form of the receptor, the protein was expressed using a baculovirus expression system. Clone 7 was missing about 350 base pairs of coding sequence at the 5' end. This region was cloned by PCR using the primers described above and in Example 1. A clone containing the complete coding region of sVEGF-RI was constructed by combining the 5' PCR fragment with sVEGF-RI clone 7 which overlapped at a SacI site. The 5' EcoRi site was then changed to a BamHI site and the full length sVEGF-RI was cloned into pBluebac III (Invitrogen) as a BamHI/BamHI fragment. A recombinant baculovirus P-3 stock containing the sVEGF-RI gene 3' in relation to the polyhedrin promoter was then prepared as described herein.

Figure 4:
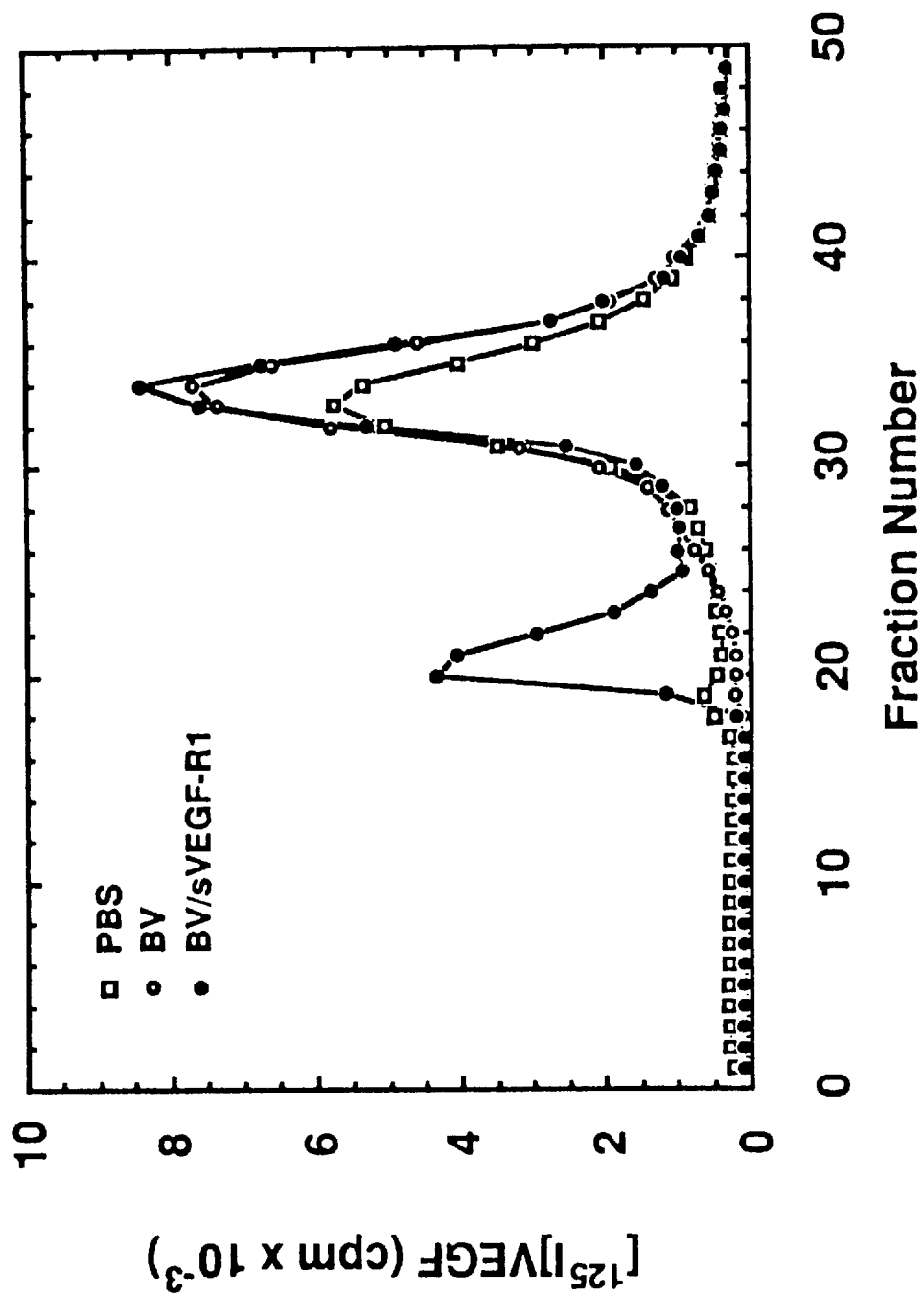
FIG. 4—Demonstration that recombinant host cells express sVEGF-RI is shown by the formation of high molecular weight complexes of sVEGF-RI and [$^{125}$I]VEGF and separated by size exclusion chromatography.

Culture media from small scale infections were tested for the ability to form high molecular weight complexes with [$^{125}$I]VEGF. The labeled ligand and culture media from the baculovirus infected cells were combined and incubated. The reactions were then analyzed by size exclusion chromatography. When the wild-type infected culture medium was mixed with the radioactive ligand (FIG. 4) a single radioactive peak was observed. However, when the sVEGF-RI infected culture medium was used, a high molecular weight complex was formed, as evident by the appearance of a second peak in this reaction eluting near the void volume of the column. This experiment showed that the natural soluble form of the FLT VEGF receptor, sVEGF-RI, forms a high molecular weight complex with VEGF.

The recombinantly produced sVEGF-R is purified from the recombinant host cell extracts or cell culture fluid using heparin-sepharose column chromatography which specifically binds the sVEGF-R protein. The heparin-sepharose bound VEGF-R column is washed using a suitable buffer containing between 0.1M and 0.6M NaCl which removes contaminating proteins without significant loss of sVEGF-R. The sVEGF-R is eluted from the heparin-sepharose column using a suitable buffer containing about 1M NaCl, yielding substantially purified sVEGF-R.

Binding of the sVEGF-RI to VEGF - The binding of $^{125}$I-labelled VEGF to sVEGF-RI was characterized by crosslinking, and by complex formation with sVEGF-RI absorbed to 96 well plates.

Figure 6:
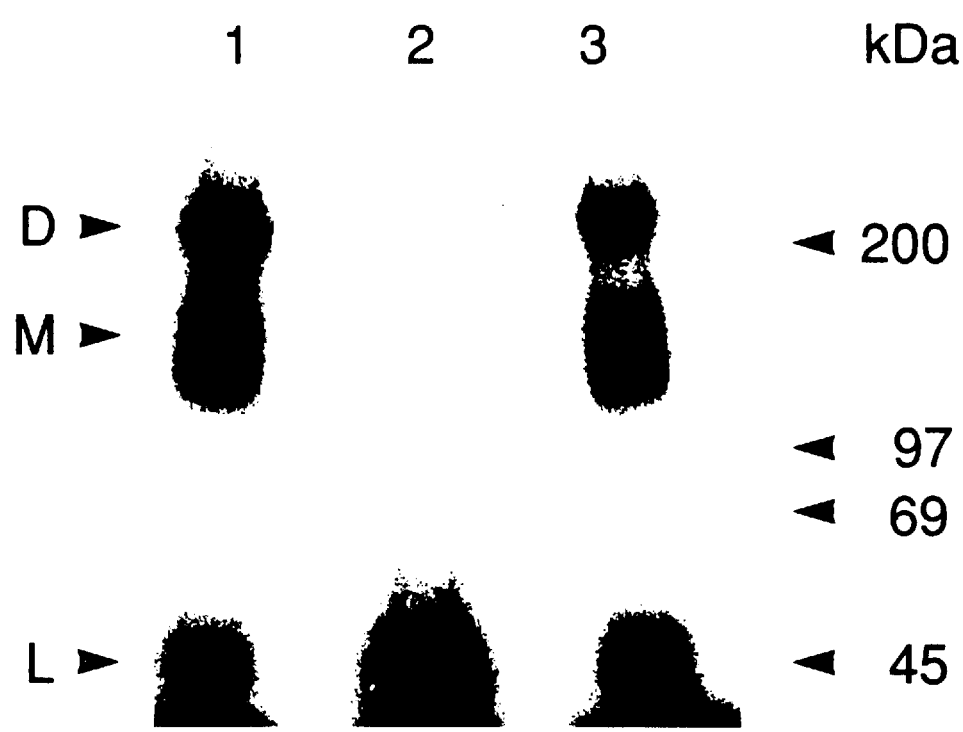
FIG. 6—Cross-linked products of sVEGF-RI and [$^{125}$I] VEGF are shown at about 145 kDa, and at about 245 kDa.

The crosslinked products are shown in FIG. 6. The sVEGF-RI was cross-linked to [$^{125}$I]VEGF (lane 1); in the presence of unlabelled VEGF (lane 2) and unlabelled bFGF (lane 3). Two high molecular weight bands (about 145 kDa and 245 kDa) were formed in the sVEGF-RI and [$^{125}$I] VEGF containing reaction, and in the sVEGF-RI and [$^{125}$I] VEGF plus an excess of unlabelled bFGF reaction. The two high molecular weight bands were not present when sVEGF-RI was incubated with [$^{125}$1]VEGF plus an excess of unlabelled VEGF, demonstrating the specificity of sVEGF-RI for VEGF, and the ability of sVEGF-RI to form a dimer. The 145 kDa band is presumably a crosslinked complex containing one receptor molecule (about 100 kDa) and a VEGF dimer (about 46 kDa). As shown in FIG. 6 complexes containing two receptor molecules (about 245 kDA) were also observed. This suggests that each VEGF dimer can bind one or two receptor molecules and that the soluble form of the VEGF receptor may undergo ligand-induced dimerization.

Figure 7A:
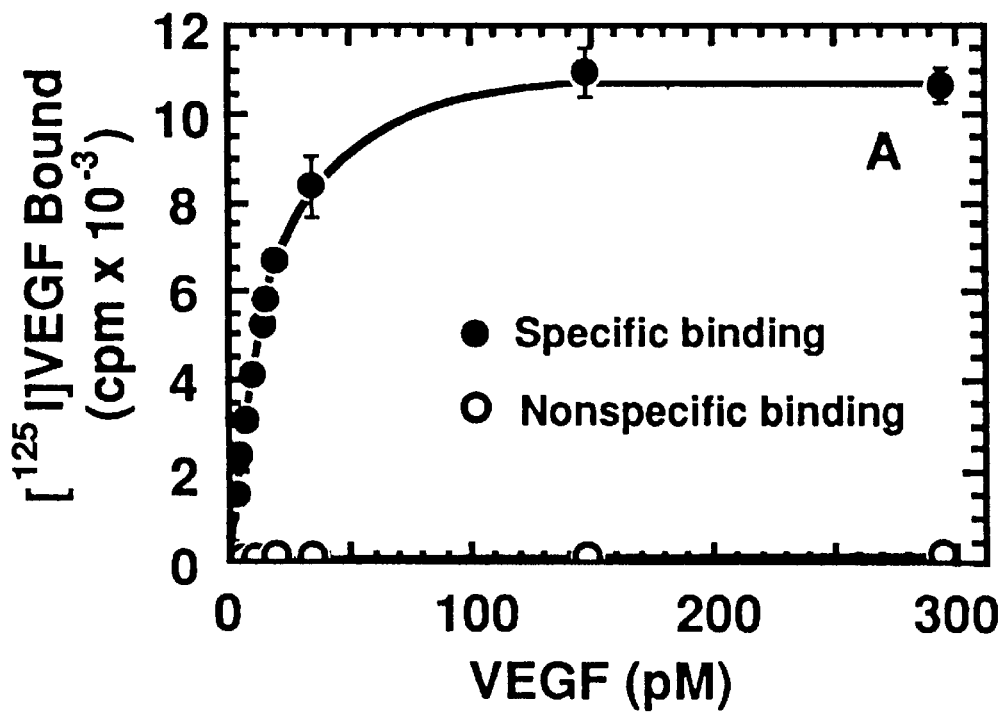
FIG. 7A—Analysis of specific and nonspecific binding of VEGF to sVEGF-RI.
Figure 7B:
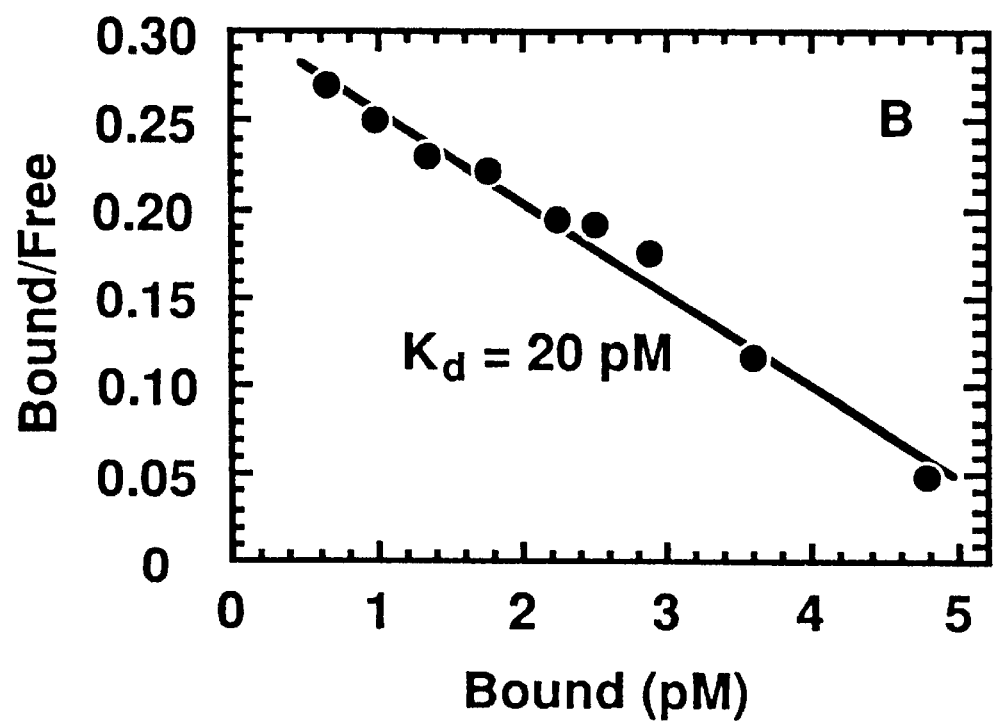
FIG. 7B—Scatchard plot analysis of VEGF binding to sVEGF-RI from FIG. 7A.

The affinity of sVEGF-RI for VEGF was evaluated by absorbing sVEGF-RI to the surface of a 96 well plate, followed by blocking the nonspecific sites with 0.5% gelatin. Variable amounts of labeled ligand were added to each well (FIG. 7A). These results demonstrate that sVEGF-RI binds VEGF with high affinity with an apparent $K_d$ of about 20 pM (FIG. 7B). Since the soluble form of the receptor is missing the Ig domain closest to the transmembrane spanning region, this domain is not required for ligand binding.

The sVEGF-RI is shown to inhibit binding of VEGF to HUVECs by incubating cultured HUVECs with [$^{125}$I]VEGF and various amounts of sVEGF-RI. Following incubation, the cells are washed to remove unbound [$^{125}$I]VEGF. The cells are then solubilized and the amount of cell-associated $^{125}$I is determined by gamma counter, which demonstrates the amount of [$^{125}$I]VEGF which was capable of binding to the cellular VEGF receptor in the presence of sVEGF-RI. Using this method, it is demonstrated that sVEGF-RI was capable of inhibiting [$^{125}$I]VEGF binding to HUVECs VEGF receptor (see FIG. 8).

Figure 9:
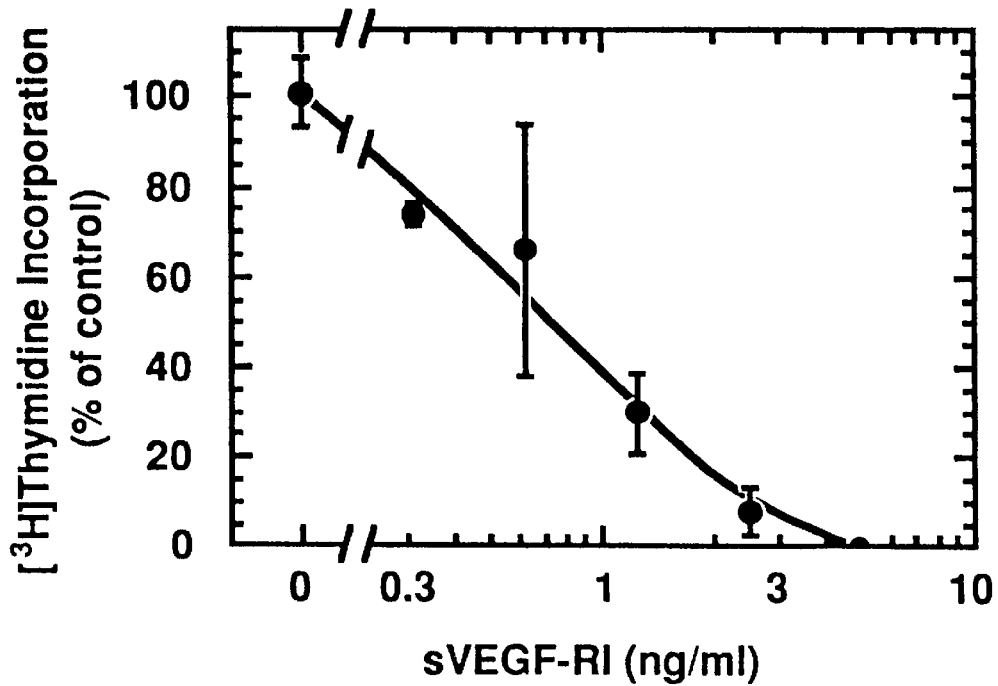
FIG. 9—Inhibition of VEGF-mediated mitogenesis on HUVECs is shown using sVEGF-RI.

Since sVEGF-RI was able to inhibit VEGF binding to cell receptors, it was then determined that sVEGF-RI could inhibit VEGF induced mitogenesis. Cells are preincubated with sVEGF-RI and then incubated with VEGF in the presence of [$^3$H]thymidine. Following incubation, the amount of cellular DNA-incorporated [$^3$H]thymidine is measured which indicates whether VEGF has induced mitogenesis and caused [$^3$H]thymidine to be incorporated into cellular DNA. The presence of sVEGF-RI inhibits the ability of VEGF to stimulate mitogenesis as shown in FIG. 9.

The inhibitor of the present invention can be used for the inhibition of VEGF activity. The inhibitor can be used either topically or intravascularly. For topical applications the formulation would be applied directly at a rate of about 10 ng to about 1 mg/cm$^2$/day. For intravaneous applications, the inhibitor is used at a rate of about 1 mg to about 10 mg/kg/day of body weight. For internal use, the formulation may be released directly into the region to be treated either from implanted slow release polymeric material or from slow release pumps or repeated injections. The release rate in either case is about 100 ng to about 100 mg/day/cm$^3$.

For non-topical application the VEGF inhibitor is administered in combination with pharmaceutically acceptable carriers or diluents such as phosphate buffer, saline, phosphate buffered saline, Ringer's solution, and the like, in a pharmaceutical composition, according to standard pharmaceutical practice. For topical application, various pharmaceutical formulations are useful for the administration of the active compound of this invention. Such formulations include, but are not limited to, the following: ointments such as hydrophilic petrolatum or polyethylene glycol ointment; pastes which may contain gums such as xanthan gum; solutions such as alcoholic or aqueous solutions; gels such as aluminum hydroxide or sodium alginate gels; albumins such as human or animal albumins; collagens such as human or animal collagens; celluloses such as alkyl celluloses, hydroxy alkyl celluloses and alkylhydroxyalkyl celluloses, for example methylcellulose, hydroxyethyl cellulose, carboxymethyl cellulose, hydroxypropyl methylcellulose, and hydroxypropyl cellulose; polyoxamers such as Pluronic® Polyols exemplified by Pluronic® F-127; tetronics such as tetronic 1508; and alginates such as sodium alginate.

The following examples are provided as illustrative of the present invention without, however, limiting the same thereto.

EXAMPLE 1

Cloning fit-related sVEGF-RI - A 580 base pair DNA probe for fit was obtained by PCR of the HUVEC phage library using the primers 5' GCACCTTGGTTGTGGCT-GAC 3' (SEQ. ID. No.: 1) and 5' TGGAATTCGTGCTGCT-TCCTGGTCC 3'(SEQ. ID. No.: 2). The resulting DNA fragment was cloned into pGEM3Z as a XbaI/EcoRI fragment. The probe was prepared by the random priming method [Feinberg, A. P. and Vogelstein, B., (1983) Anal.Biochem., 132, pp.6–13] using the megaprime kit (Amersham) at a specific activity of 1×10$^7$ cpm/ng. The HUVEC cDNA library was plated at a density of 5×10$^4$ plaques/150 cm plate then about 1×10$^6$ plaques were screened by hybridization as previously described [Maniatis, T. et al., supra]. Briefly, following prehybridization at 42° C. for 2 hours in 50% formamide, 5X SSC, 5X Denhardt's solution, 0.1% SDS, 100 mg/ml salmon sperm DNA (hybridization buffer) the filters were hybridized with the probe for 16 hours at 42° C. in hybridization buffer. The filters were washed one time for 15 min at room temperature in 2X SSC then three times at 55° C. in 0.1 X SSC. Four positive plaques were identified and rescreened two additional times to obtain homogeneous isolates. Inserts were cloned into pGEM3Z for DNA sequence analysis. Two of these clones were identified which contained less than the full length fit coding region. DNA sequence analysis showed that these clones lacked the 5' coding region of fit. The DNA sequence is shown in Table 1 and FIG. 2, and the deduced amino acid sequence is shown in Table 2 and FIG. 3. The 5' end of fit was cloned by PCR using the primers 5' GGAAT-TCCGCGCTCACCATGGTCAGC 3'(SEQ.ID.NO.:3) and 5' TTTGAATTCACCCGGCAGGGAATGACG 3' (SEQ.ID.NO.:4). The PCR fragment generated with this set of primers was cloned into fit clone 7 as an EcoRi/SacI fragment.

TABLE 1

GCGGACACTCCTCTCGGCTCCTCCCCGGCAGCGGCGGCGGCTCG

GAGCGGGCTCCGGGGCTCGGGTGCAGCGGCCAGCGGGCCTGGC

GGCGAGGATTACCCGGGGAAGTGGTTGTCTCCTGGCTGGAGCC

GCGAGACGGGCGCTCAGGGCGCGGGGCCGGCGGCGGCGAACG

AGAGGACGGACTCTGGCGGCCGGGTCGTTGGCCGGGGGAGCGC

GGGCACCGGGCGAGCAGGCCGCGTCGCGCTCACC ATG GTC

AGC TAC TGG GAC ACC GGG GTC CTG CTG TGC GCG CTG

CTC AGC TGT CTG CTT CTC ACA GGA TCT AGT TCA GGT TCA

AAA TTA AAA GAT CCT GAA CTG AGT TTA AAA GGC ACC

CAG CAC ATC ATG CAA GCA GGC CAG ACA CTG CAT CTC

CAA TGC AGG GGG GAA GCA GCC CAT AAA TGG TCT TTG

CCT GAA ATG GTG AGT AAG GAA AGC GAA AGG CTG AGC

ATA ACT AAA TCT GCC TGT GGA AGA AAT GGC AAA CAA

TTC TGC AGT ACT TTA ACC TTG AAC ACA GCT CAA GCA

AAC CAC ACT GGC TTC TAC AGC TGC AAA TAT CTA GCT

TABLE 1-continued

```
GTA CCT ACT TCA AAG AAG AAG GAA ACA GAA TCT GCA

ATC TAT ATA TTT ATT AGT GAT ACA GGT AGA CCT TTC

GTA GAG ATG TAC AGT GAA ATC CCC GAA ATT ATA CAC

ATG ACT GAA GGA AGG GAG CTC GTC ATT CCC TGC CGG

GTT ACG TCA CCT AAC ATC ACT GTT ACT TTA AAA AAG

TTT CCA CTT GAC ACT TTG ATC CCT GAT GGA AAA CGC

ATA ATC TGG GAC AGT AGA AAG GGC TTC ATC ATA TCA

AAT GCA ACG TAC AAA GAA ATA GGG CTT CTG ACC TGT

GAA GCA ACA GTC AAT GGG CAT TTG TAT AAG ACA AAC

TAT CTC ACA CAT CGA CAA ACC AAT ACA ATC ATA GAT

GTC CAA ATA AGC ACA CCA CGC CCA GTC AAA TTA CTT

AGA GGC CAT ACT CTT GTC CTC AAT TGT ACT GCT ACC ACT

CCC TTG AAC ACG AGA GTT CAA ATG ACC TGG AGT TAC

CCT GAT GAA AAA AAT AAG AGA GCT TCC GTA AGG CGA

CGA ATT GAC CAA AGC AAT TCC CAT GCC AAC ATA TTC TAC

AGT GTT CTT ACT ATT GAC AAA ATG CAG AAC AAA GAC

AAA GGA CTT TAT ACT TGT CGT GTA AGG AGT GGA CCA

TCA TTC AAA TCT GTT AAC ACC TCA GTG CAT ATA TAT GAT

AAA GCA TTC ATC ACT GTG AAA CAT CGA AAA CAG CAG

GTG CTT GAA ACC GTA GCT GGC AAG CGG TCT TAC CGG

CTC TCT ATG AAA GTG AAG GCA TTT CCC TCG CCG GAA GTT

GTA TGG TTA AAA GAT GGG TTA CCT GCG ACT GAG AAA

TCT GCT CGC TAT TTG ACT CGT GGC TAC TCG TTA ATT ATC

AAG GAC GTA ACT GAA GAG GAT GCA GGG AAT TAT ACA

ATC TTG CTG AGC ATA AAA CAG TCA AAT GTG TTT AAA

AAC CTC ACT GCC ACT CTA ATT GTC AAT GTG AAA CCC

CAG ATT TAC GAA AAG GCC GTG TCA TCG TTT CCA GAC

CCG GCT CTC TAC CCA CTG GGC AGC AGA CAA ATC CTG
```

TABLE 1-continued

ACT TGT ACC GCA TAT GGT ATC CCT CAA CCT ACA ATC

AAG TGG TTC TGG CAC CCC TGT AAC CAT AAT CAT TCC

GAA GCA AGG TGT GAC TTT TGT TCC AAT AAT GAA GAG

TCC TTT ATC CTG GAT GCT GAC AGC AAC ATG GGA AAC

AGA ATT GAG AGC ATC ACT CAG CGC ATG GCA ATA ATA

GAA GGA AAG AAT AAG ATG GCT AGC ACC TTG GTT GTG

GCT GAC TCT AGA ATT TCT GGA ATC TAC ATT TGC ATA

GCT TCC AAT AAA GTT GGG ACT GTG GGA AGA AAC ATA

AGC TTT TAT ATC ACA GAT GTG CCA AAT GGG TTT CAT

GTT AAC TTG GAA AAA ATG CCG ACG GAA GGA GAG GAC

CTG AAA CTG TCT TGC ACA GTT AAC AAG TTC TTA TAC

AGA GAC GTT ACT TGG ATT TTA CTG CGG ACA GTT AAT

AAC AGA ACA ATG CAC TAC AGT ATT AGC AAG CAA AAA

ATG GCC ATC ACT AAG GAG CAC TCC ATC ACT CTT AAT

CTT ACC ATC ATG AAT GTT TCC CTG CAA GAT TCA GGC

ACC TAT GCC TGC AGA GCC AGG AAT GTA TAC ACA GGG

GAA GAA ATC CTC CAG AAG AAA GAA ATT ACA ATC AGA

GGT GAG CAC TGC AAC AAA AAG GCT GTT TTC TCT CGG

ATC TCC AAA TTT AAA AGC ACA AGG AAT GAT TGT ACC

ACACAAAGTAATGTAAAACATTAAAGGACTCATTAAAAAGTA

ACAGTTGTCTCATATCATCTTGATTTATTGTCACTGTTGCTAAC

TTTCAGGCTCGGAGGAGATGCTCCTCCCAAAATGAGTTCGGAG

ATGATAGCAGTAATAATGAGACCCCCGGGCTCCAGCTCTGGGC

CCCCCATTCAGGCCGAGGGGGCTGCTCCGGGGGGCCGACTTGG

TGCACGTTTGGATTTGGAGGATCCCTGCACTGCCTTCTCTGTGT

TTGTTGCTCTTGCTGTTTTCTCCTGCCTGATAAACAACAACTTG

GGATGATCCTTTCCATTTTGATGCCAACCTCTTTTTATTTTTAA

GCGGCGCCCTATAGT (SEQ. ID. NO.: 5)

TABLE 2

| | | | | | | | | | | | | | | | |
|---|---|---|---|---|---|---|---|---|---|---|---|---|---|---|---|
| Met | Val | Ser | Tyr | Trp | Asp | Thr | Gly | Val | Leu | Leu | Cys | Ala | Leu | Leu | Ser |
| Cys | Leu | Leu | Leu | Thr | Gly | Ser | Ser | Ser | Gly | Ser | Lys | Leu | Lys | Asp | Pro |
| Glu | Leu | Ser | Leu | Lys | Gly | Thr | Gln | His | Ile | Met | Gln | Ala | Gly | Gln | Thr |
| Leu | His | Leu | Gln | Cys | Arg | Gly | Glu | Ala | Ala | His | Lys | Trp | Ser | Leu | Pro |
| Glu | Met | Val | Ser | Lys | Glu | Ser | Glu | Arg | Leu | Ser | Ile | Thr | Lys | Ser | Ala | Cys |
| Gly | Arg | Asn | Gly | Lys | Gln | Phe | Cys | Ser | Thr | Leu | Thr | Leu | Asn | Thr | Ala |
| Gln | Ala | Asn | His | Thr | Gly | Phe | Tyr | Ser | Cys | Lys | Tyr | Leu | Ala | Val | Pro |
| Thr | Ser | Lys | Lys | Lys | Glu | Thr | Glu | Ser | Ala | Ile | Tyr | Ile | Phe | Ile | Ser | Asp |
| Thr | Gly | Arg | Pro | Phe | Val | Glu | Met | Tyr | Ser | Glu | Ile | Pro | Glu | Ile | Ile | His |
| Met | Thr | Glu | Gly | Arg | Glu | Leu | Val | Ile | Pro | Cys | Arg | Val | Thr | Ser | Pro |
| Asn | Ile | Thr | Val | Thr | Leu | Lys | Lys | Phe | Pro | Leu | Asp | Thr | Leu | Ile | Pro |
| Asp | Gly | Lys | Arg | Ile | Ile | Trp | Asp | Ser | Arg | Lys | Gly | Phe | Ile | Ile | Ser | Asn |
| Ala | Thr | Tyr | Lys | Glu | Ile | Gly | Leu | Leu | Thr | Cys | Glu | Ala | Thr | Val | Asn |
| Gln | His | Leu | Tyr | Lys | Thr | Asn | Tyr | Leu | Thr | His | Arg | Gln | Thr | Asn | Thr |
| Ile | Ile | Asp | Val | Gln | Ile | Ser | Thr | Pro | Arg | Pro | Val | Lys | Leu | Leu | Arg | Gly |
| His | Thr | Leu | Val | Leu | Asn | Cys | Thr | Ala | Thr | Thr | Pro | Leu | Asn | Thr | Arg |
| Val | Gln | Met | Thr | Trp | Ser | Tyr | Pro | Asp | Glu | Lys | Asn | Lys | Arg | Ala | Ser |
| Val | Arg | Arg | Arg | Ile | Asp | Gln | Ser | Asn | Ser | His | Ala | Asn | Ile | Phe | Tyr | Ser |
| Val | Leu | Thr | Ile | Asp | Lys | Met | Gln | Asn | Lys | Asp | Lys | Gly | Leu | Tyr | Thr |
| Cys | Arg | Val | Arg | Ser | Gly | Pro | Ser | Phe | Lys | Ser | Val | Asn | Thr | Ser | Val | His |
| Ile | Tyr | Asp | Lys | Ala | Phe | Ile | Thr | Val | Lys | His | Arg | Lys | Gln | Gln | Val | Leu |
| Glu | Thr | Val | Ala | Gly | Lys | Arg | Ser | Tyr | Arg | Leu | ser | Met | Lys | Val | Lys |
| Ala | Phe | Pro | Ser | Pro | Glu | Val | Val | Trp | Leu | Lys | Asp | Gly | Leu | Pro | Ala |
| Thr | Glu | Lys | Ser | Ala | Arg | Tyr | Leu | Thr | Arg | Gly | Tyr | Ser | Leu | Ile | Ile | Lys |
| Asp | Val | Thr | Glu | Glu | Asp | Ala | Gly | Asn | Tyr | Thr | Ile | Leu | Leu | Ser | Ile | Lys |
| Gln | Ser | Asn | Val | Phe | Lys | Asn | Leu | Thr | Ala | Thr | Leu | Ile | Val | Asn | Val |
| Lys | Pro | Gln | Ile | Tyr | Glu | Lys | Ala | Val | Ser | Ser | Phe | Pro | Asp | Pro | Ala | Leu |
| Tyr | Pro | Leu | Gly | Ser | Arg | Gln | Ile | Leu | Thr | Cys | Thr | Ala | Tyr | Gly | Ile | Pro |

TABLE 2-continued

| | | | | | | | | | | | | | | | |
|---|---|---|---|---|---|---|---|---|---|---|---|---|---|---|---|
| Gln | Pro | Thr | Ile | Lys | Trp | Phe | Trp | His | Pro | Cys | Asn | His | Asn | His | Ser | Glu |
| Ala | Arg | Cys | Asp | Phe | Cys | Ser | Asn | Asn | Glu | Glu | Ser | Phe | Ile | Leu | Asp |
| Ala | Asp | Ser | Asn | Met | Gly | Asn | Arg | Ile | Glu | Ser | Ile | Thr | Gln | Arg | Met | Ala |
| Ile | Ile | Glu | Gly | Lys | Asn | Lys | Met | Ala | Ser | Thr | Leu | Val | Val | Ala | Asp | Ser |
| Arg | Ile | Ser | Gly | Ile | Tyr | Ile | Cys | Ile | Ala | Ser | Asn | Lys | Val | Gly | Thr | Val |
| Gly | Arg | Asn | Ile | Ser | Phe | Tyr | Ile | Thr | Asp | Val | Pro | Asn | Gly | Phe | His | Val |
| Asn | Leu | Glu | Lys | Met | Pro | Thr | Glu | Gly | Glu | Asp | Leu | Lys | Leu | Ser | Cys |
| Thr | Val | Asn | Lys | Phe | Leu | Tyr | Arg | Asp | Val | Thr | Trp | Ile | Leu | Leu | Arg |
| Thr | Val | Asn | Asn | Arg | Thr | Met | His | Tyr | Ser | Ile | Ser | Lys | Gln | Lys | Met |
| Ala | Ile | Thr | Lys | Glu | His | Ser | Ile | Thr | Leu | Asn | Leu | Thr | Ile | Met | Asn | Val |
| Ser | Leu | Gln | Asp | Ser | Gly | Thr | Tyr | Ala | Cys | Arg | Ala | Arg | Asn | Val | Tyr |
| Thr | Gly | Glu | Glu | Ile | Leu | Gln | Lys | Lys | Glu | Ile | Thr | Ile | Arg | Gly | Glu | His |
| Cys | Asn | Lys | Lys | Ala | Val | Phe | Ser | Arg | Ile | Ser | Lys | Phe | Lys | Ser | Thr | Arg |
| Asn | Asp | Cys | Thr | Thr | Gln | Ser | Asn | Val | Lys | His ... (SEQ. ID. NO.: 6) |

EXAMPLE 2
Expression of sVEGF-RI in Sf9 insect cells

The full length sequence encoding sVEGF-RI was cloned as an EcoRI/BamHI fragment into pGEM3Z. The EcoRI site was then modified to a BamHI site and cloned into pBlueBac III 3' of the polyhedrin promoter (psFLTblue). This plasmid was transfected into Sf9 armyworm cells using liposomes. After 48 hours the medium from the transfected cells which contains recombinant polyhedrin virus particles, was harvested. Dilutions ($10^3$–$10^4$ fold) of the virus were prepared and plaque purified in soft agar containing 150 mg/ml 5-bromo-4-chloro-3-indolyl-B-D-galactoside. Recombinant plaques were identified by blue color and used to infect Sf9 cells ($5 \times 10^5$ cells/well) in 12 well plates. Medium (100 ml) from polyhedrin minus infections was used to prepare P-2 viral stocks by infecting $2.5 \times 10^6$ cells in a T-25 flask. Large scale high titer P-3 viral stocks were then prepared by infecting Sf9 cells (500 ml at $2 \times 10^6$ cells/ml) with 5 ml of the P-2 stock then incubating at 27° C. for 5–6 days and the medium was harvested by centrifugation. Protein expression was accomplished by infecting cells at a density of 2–$2.5 \times 10^6$ cells/ml with a multiplicity of infection of 5–10. Twenty four hours after infection the cells were changed to a serum free medium (SF90011I, Gibco BRL), incubated for an additional 48 hours and the medium was collected. This conditioned medium contains the recombinantly expressed sVEGF-RI protein.

EXAMPLE 3
Iodination of VEGF and PIGF $^{125}$I-labeled human recombinant VEGF was prepared by the chloramine T method (Hunter, W. M. and Greenwood, F. C., (1962) Nature (London), 194, pp. 495–496). Briefly, 1 mg of VEGF in 30% acetonitrile/0.1% trifluroacetic acid was adjusted to pH 7.1 by the addition of ⅓ volume of 0.4M sodium phosphate buffer, pH 7.1. Freshly dissolved chloramine T (4 ml of a 2 mg/ml stock in 0.1M sodium phosphate buffer, pH 7.1) was added to the VEGF solution and reacted for 45 seconds at room temperature (total volume of 150 ml). The reaction was stopped by the addition of 50 ml of 10 mM KI and 50 ml of 2 mg/ml meta bisufite. The labeled ligand was separated from the free $^{125}$I by gel filtration on a 0.7×15 cm Sephadex G-25 column equilibrated in PBS with 1 mg/ml gelatin. Fractions were counted in a Packard g counter, aliquoted and stored at −70° C. VEGF was labeled to a specific activity of $5 \times 10^5$ to $1 \times 10^6$ cpm/ng. Recombinant human PlGF was iodinated by the chloramine-T method as described herein, to specific activity between approximately $3 \times 10^5$–$9 \times 10^5$ cpm/ng. After iodination, PlGF was stored at 4° C. in PBS containing 1 mg/ml gelatin.

Gel Filtration Chromatography

Receptor-ligand complex was formed by incubating 10 ml of $^{125}$I-labeled VEGF (105 cpm) with 100 ml of either wild-type or baculovirus sVEGF-RI-containing, infected Sf9 cell culture medium overnight at room temperature. The reaction products were separated on a Sephacryl S200 gel filtration column (0.7×25 cm) equilibrated in PBS, 1 mg/ml gelatin, at a flow rate of 15 ml/hr. Fractions (0.75 ml) were collected and analyzed in a g counter. Receptor-ligand complexes pass quickly through the column while the free labelled VEGF passes through more slowly. The results of this experiment shown in FIG. 4 demonstrate the formation of a high molecular weight complex between labelled VEGF and sVEGF-RI protein. This shows that sVEGF-RI binds VEGF.

Crosslinking

Purified sVEGF-RI (1–10 ng) was added to 25 ml of binding buffer (Dulbecco's Modified Eagle's medium (DME), 25 mM HEPES, pH 7.5, 0.3% gelatin), and 1×10⁵ cpm of [$^{125}$I]-VEGF was added (FIG. 6, lane 1) with either 200 ng of unlabelled VEGF (lane 2) or bFGF (lane 3), then incubated 2 to 16 hours at room temperature. Bis (sulfosuccinimidyl)suberate (Pierce) crosslinker was added to a final concentration of 1 mM. The reaction was stopped after 15 min by the addition of boiling SDS PAGE sample buffer. The crosslinked products were separated by SDS PAGE on a 7.5% acrylamide gel and analyzed either by autoradiography or a phosphoimager. The results are shown in FIG. 6 and demonstrate that sVEGF-RI binds labelled VEGF by the appearance of two bands of about 145 kDa and 245 kDa. The 145 kDa band consists of one sVEGF-RI molecule and one VEGF molecule (Monomer, M.). The 245 kDa band apparently consists of two sVEGF-RI molecules and one VEGF dimer (D). Free VEGF ligand (L) dimers migrated at about 45 kDA.

Purified Ex-KDR and sFLT were each allowed to bind either [$^{125}$I]VEGF or [$^{125}$I]PlGF at 25° C. for 1 hr in a final volume of 25 μl in binding buffer (10 mM Hepes, pH 7.4, 0.01% BSA, 100 mM NaCl) with or without an excess of the appropriate unlabeled ligand. Competition binding was accomplished by incubation in the presence of various concentrations of unlabeled VEGF (0.1–400 nM). The reactions were then crosslinked with 1 mM BS³ at 25° C. for 15 min followed by the addition of boiling Laemmli sample buffer (10). The crosslinked products were analyzed by SDSP7.5% PAGE and the complexes were visualized using a PhosphoImager (Molecular Dynamics, Sunnyvale, Calif.). In the competition crosslinking experiments the amount of radioactivity contained in the Ex-KDR/[$^{125}$I]VEGF complex as well as the uncomplexed [$^{125}$I]VEGF were quantified using the PhosphoImager.

Binding assay

The binding of sVEGF-RI to VEGF was analyzed using a 96 well plate assay as described by Duan, D-S. R. et al., supra. Briefly, sVEGF-RI, 50 to 200 ml partially purified by Mono Q chromatography (Pharmacia), was diluted to 10 ml in 25 mM TRIS, pH 7.4, 100 mM NaCl, 20 mM NH₄HCO₃. Aliquots (100 ml) were absorbed to the surface of a 96 well plate for 18 hours at 4° C., the plates were then washed twice with blocking buffer (DME, 25 mM HEPES, pH 7.5, 0.5% gelatin) and the nonspecific sites were blocked in the same buffer for 6 hours at 4° C. The plate was then washed twice in binding buffer. Various amounts of [$^{125}$I]VEGF were added to the wells in a final volume of 100 ml/well and incubated for 2 hours at room temperature. The wells were washed three times with 100 ml of binding buffer, the bound protein was solubilized with 100 ml of 1% SDS, 0.5% BSA and counted in a g counter. The results, shown in FIG. 7A; were analyzed by the method of Scatchard [Scatchard, G., (1949) Ann. N.Y. Acad. Sci., 51, pp. 660–672]. The analysis demonstrates that sVEGF-RI retains high affinity binding for VEGF with a $K_d$ value of about 20 pM (FIG. 7B). This clearly demonstrates that sVEGF-RI, lacking the transmembrane region and adjacent Ig-like domain, binds VEGF with high affinity and that these regions are not required for VEGF binding.

Purified Ex-KDR and sFLT were each allowed to bind either [$^{125}$I]VEGF or [$^{125}$I]PlGF at 25° C. for 1 hour in a final volume of 25 μl in binding buffer (10 mM Hepes, pH 7.4, 0.01% BSA, 100 mM NaCl) with or without an excess of the appropriate unlabeled ligand. Competition binding was accomplished by incubation in the presence of various concentrations of unlabeled VEGF (0.1–400 nM). The reactions were then crosslinked with 1 mM BS³ at 25° C. for 15 min followed by the addition of boiling Laemmli sample buffer. The crosslinked products were analyzed by SDS/ 7.5% PAGE and the complexes were visualized using a Phosphohnager (Molecular Dynamics, Sunnyvale, Calif.). In the competition crosslinking experiments the amount of radioactivity contained in the Ex-KDR/[$^{125}$I]VEGF complex as well as the uncomplexed [$^{125}$I]VEGF were quantified using the PhosphoImager.

To determine if sFLT and Ex-KDR bind VEGF and PlGF with high affinity, purified sFLT and Ex-KDR were each incubated with either [$^{125}$I]VEGF or [$^{125}$I]PlGF, covalently crosslinked and high molecular mass complexes were resolved by SDS/PAGE. sFLT formed high molecular mass complexes with both VEGF and PlGF whereas Ex-KDR formed complexes with VEGF but not with PlGF. The positions of the monomer (one VEGF dimer bound to one receptor molecule) and dimer (one VEGF dimer bound to two receptor molecules) were as expected. These radiolabeled complexes were competed by an excess of the same unlabeled VEGF or PlGF and thus are specific. PlGF was able to compete for VEGF binding to the sFLT receptor and VEGF competes for PlGF binding to this receptor. PlGF was not able to compete for [$^{125}$I]VEGF binding to Ex-KDR.

The affinity of VEGF for Ex-KDR was determined by a crosslinking competition binding assay since the Ex-KDR receptor binds poorly to 96 well plates. A constant amount of [$^{125}$I]VEGF was bound to Ex-KDR in the presence of increasing concentrations of unlabeled VEGF. The concentration of unlabeled VEGF required to displace 50% of the total [$^{125}$I]VEGF binding is approximately 1 nM, which is similar to the apparent $K_d$ for the membrane form of KDR.

Competition between PlGF and VEGF for binding to sFLT

Competitive binding of VEGF and PlGF to sFLT was analyzed by the 96 well plate binding assay. A constant amount of either [$^{125}$I]VEGF or [$^{125}$I]PlGF was bound to immobilized sFLT in the presence of increasing amounts of either unlabeled VEGF or PlGF. In comparison, 50% of the binding of [$^{125}$I]PlGF to sFLT was displaced by only 10 pM of VEGF. Approximately 110 pM of unlabeled PlGF displaced 50% of [$^{125}$I]PlGF binding to sFLT in agreement with saturation binding experiments. However, an approximately 5-fold higher concentration of PlGF (~550 pM) was required to displace 50% of the [$^{125}$I]VEGF binding to sFLT. These data indicate that VEGF and PlGF compete for the same site on sFLT at which VEGF binds with ~4-fold higher affinity than PlGF. Crosslinking competition experiments with sFLT gave similar results.

Here we show that VEGF binds to the extracellular domains of both FLT and KDR with high affinity. PlGF, however, only binds to the extracellular domain of FLT with high affinity and does not bind to the equivalent extracellular region of KDR. VEGF is able to compete efficiently for PlGF binding to sFLT whereas PlGF competes less efficiently for VEGF binding. These binding data demonstrate that VEGF complexes with sFLT somewhat tighter than does PlGF. Competitive binding infers that the VEGF and PlGF sites on sFLT are probably either overlapping or identical. Thus, sFLT will inhibit both PlGF and VEGF function.

EXAMPLE 4

Inhibition of VEGF binding by sVEGF-RI

The ability of sVEGF-RI to inhibit VEGF binding to HUVECs was tested. HUVECs were plated at 50,000 cells/ well in 24 well plates precoated with gelatin, and allowed to grow to confluence. A constant amount of [$^{125}$I]VEGF (100,000 cpm) was mixed with various amounts of partially purified sVEGF-RI in binding buffer, in a total volume of 200 μl and preincubated at room temperature for 1 hour. Samples were added to the cells and incubated for 4 hours at 4° C. with shaking. The medium was then aspirated and the cells were washed three times with binding buffer. The bound radioactivity was solubilized with 50 mM TRIS-HCl, pH 8.0, 150 mM NaCl, 1% NP40, 1% BSA and counted in a γ counter.

Figure 8:
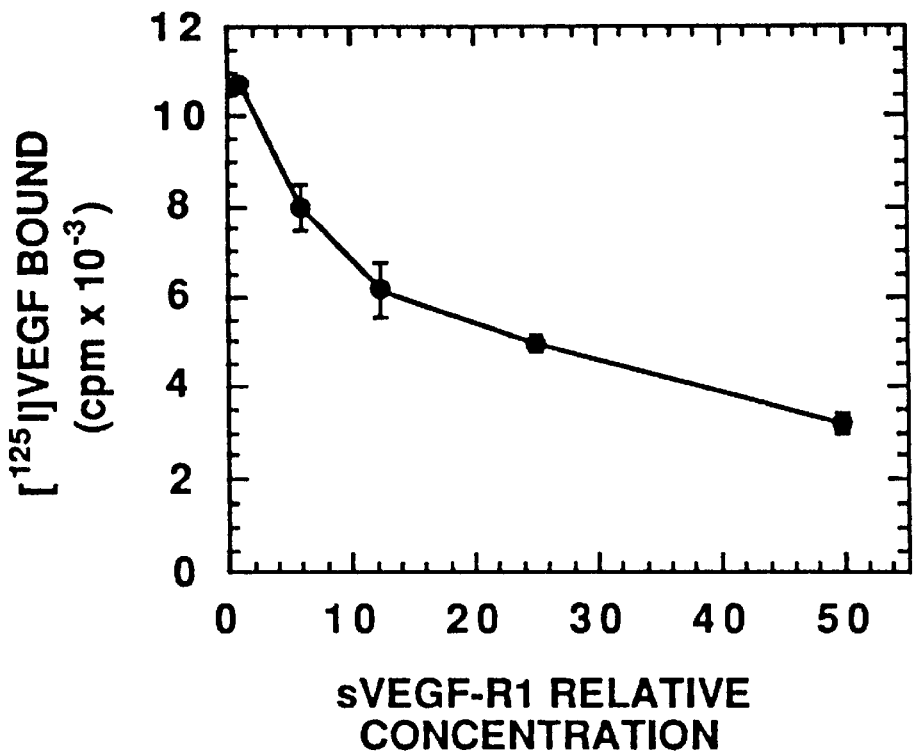
FIG. 8—Inhibition of [$^{125}$I]VEGF binding to HUVECs by sVEGF-RI is demonstrated.

The results are shown in FIG. 8. At the highest concentration of sVEGF-RI, VEGF binding to HUVECs was reduced by 70%. It may, however, be difficult to completely inhibit binding to the cellular membrane bound receptor since one molecule of sVEGF-R bound to a VEGF dimer may be able to bind to cell associated receptor to form an inactive (sVEGF-RI)-VEGP-(membrane spanning VEGF receptor) complex.

EXAMPLE 5
Inhibition of VEGF mediated mitogenesis by sVEGF-RI
Mitogenic inhibition Since sVEGF-RI was able to inhibit VEGF binding to endothelial cells, it was then determined that the soluble receptor could inhibit VEGF induced mitogenesis in HUVECs. HUVECs were plated in gelatin coated 96 well plates at a density of 4000 cells/well in 100 ml of DME supplemented with 10% heat inactivated fetal calf serum plus antibiotics (penicillin G, 100 units/ml; streptomycin sulfate, 100 mg/ml). After 16 hours the medium was changed and test samples were added, cells were preincubated with a variable amount of purified sVEGF-RI for 15 minutes at 37° C. before growth factor (10 ng/ml) was added. The cells were incubated for 24 hours then [methyl-$^3$H]thymidine (0.8 mCi/well; 20 Ci/mmol: 1Ci=37 GBq, final specific activity of 0.8 mCi/nmole) was added followed by incubated for an additional 72 hours at 37° C. under 5% $CO_2$. The cells were then washed twice with Hank's balanced salt solution adjusted to pH 7.5 with 25 mM Hepes, 0.1% BSA. The cells were then lysed, the DNA was solubilized with 0.2M $Na2CO_3$, 0.1M NaOH, and [$^3$H] thymidine incorporation was quantified by scintillation counting. The results are shown in FIG. 9. sVEGF-RI was able to completely inhibit VEGF induced [$^3$H]thymidine incorporation in HUVECs.

EXAMPLE 6
Purification of baculovirus expressed sVEGF-RI from Sf9 cells

Figure 5:
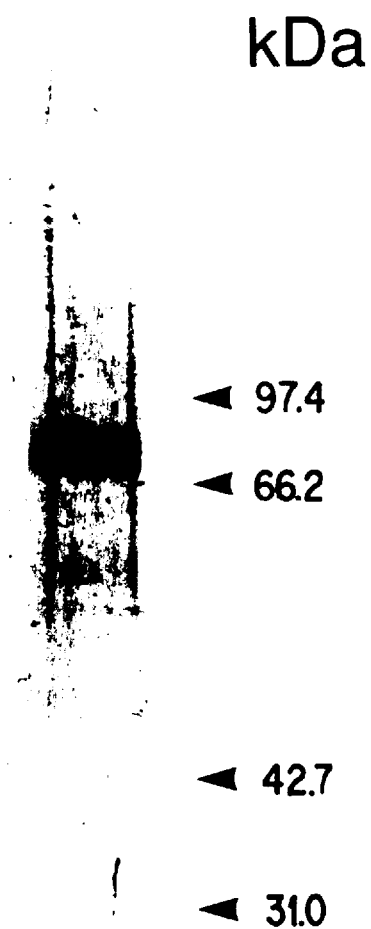
FIG. 5—A 12.5% polyacrylamide electrophoretic gel is shown which demonstrates the high degree of purity obtained for sVEGF-RI.

Culture medium from Sf9 cells infected with a baculovirus construct designed to express sVEGF-RI Example 2) was chromatographed through a heparin Sepharose CL-6B (Pharmacia) column (0.7×4 cm). The column was washed with 5 volumes of 10 mM Na-phosphate buffer, pH 6.2, 0.1M NaCl, followed by 6 ml of 10 mM Na-phosphate buffer, pH 6.2, 0.6M NaCl. The sVEGF-RI was eluted with 10 mM Na-phosphate buffer, pH 6.2, 1.0M NaCl. Polyacrylamide gel electrophoresis was performed which demonstrated greater than 90% purity (as judged by coomassie blue staining) of the recombinantly produced sVEGF-R (FIG. 5). The identity of the protein was confirmed by N-terminal protein sequence analysis. The actual N-terminus (Ser Lys Leu ...) of the recombinant protein differs by two amino acids from that predicted by Shibuya et al., supra. (Ser-Ser-Ser...). The peptidase cleavage site in sVEGF-RI produced in Sf9 cells was between residues gly-26 and ser-27.

EXAMPLE 7
Construction of KDR-related sVEGF-R

Figure 16:
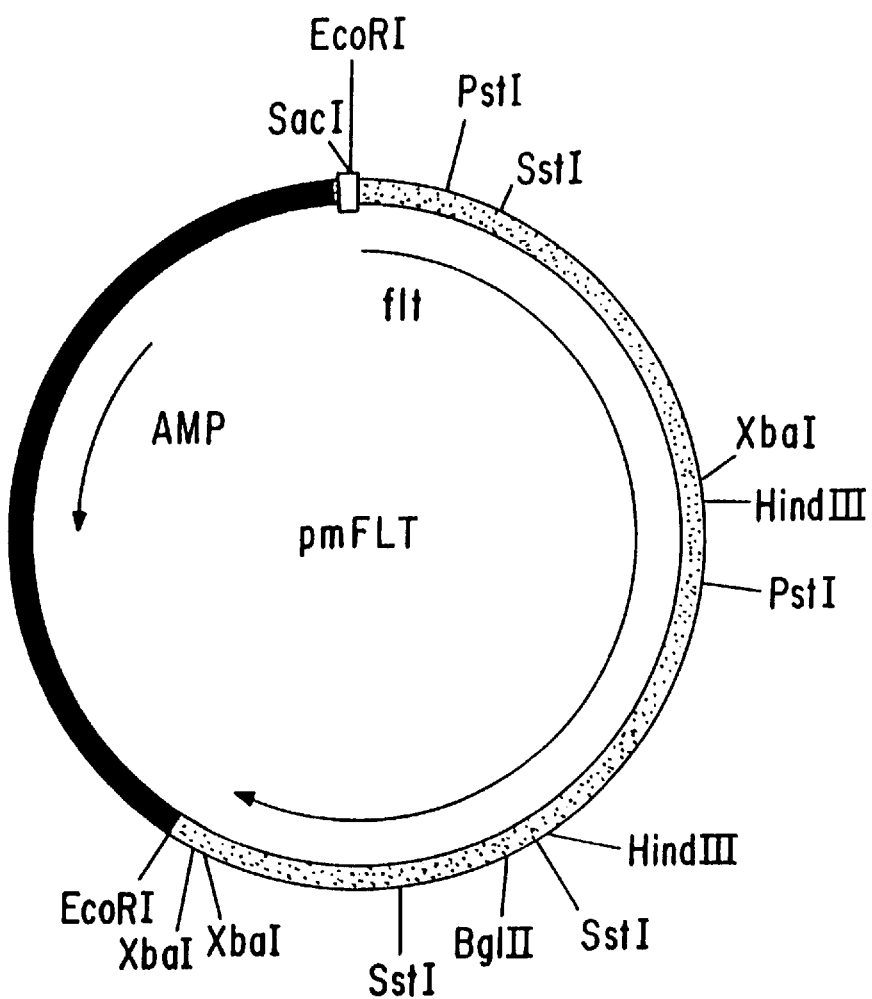
FIG. 16—A diagram of pmFLT is shown.
Figure 17:
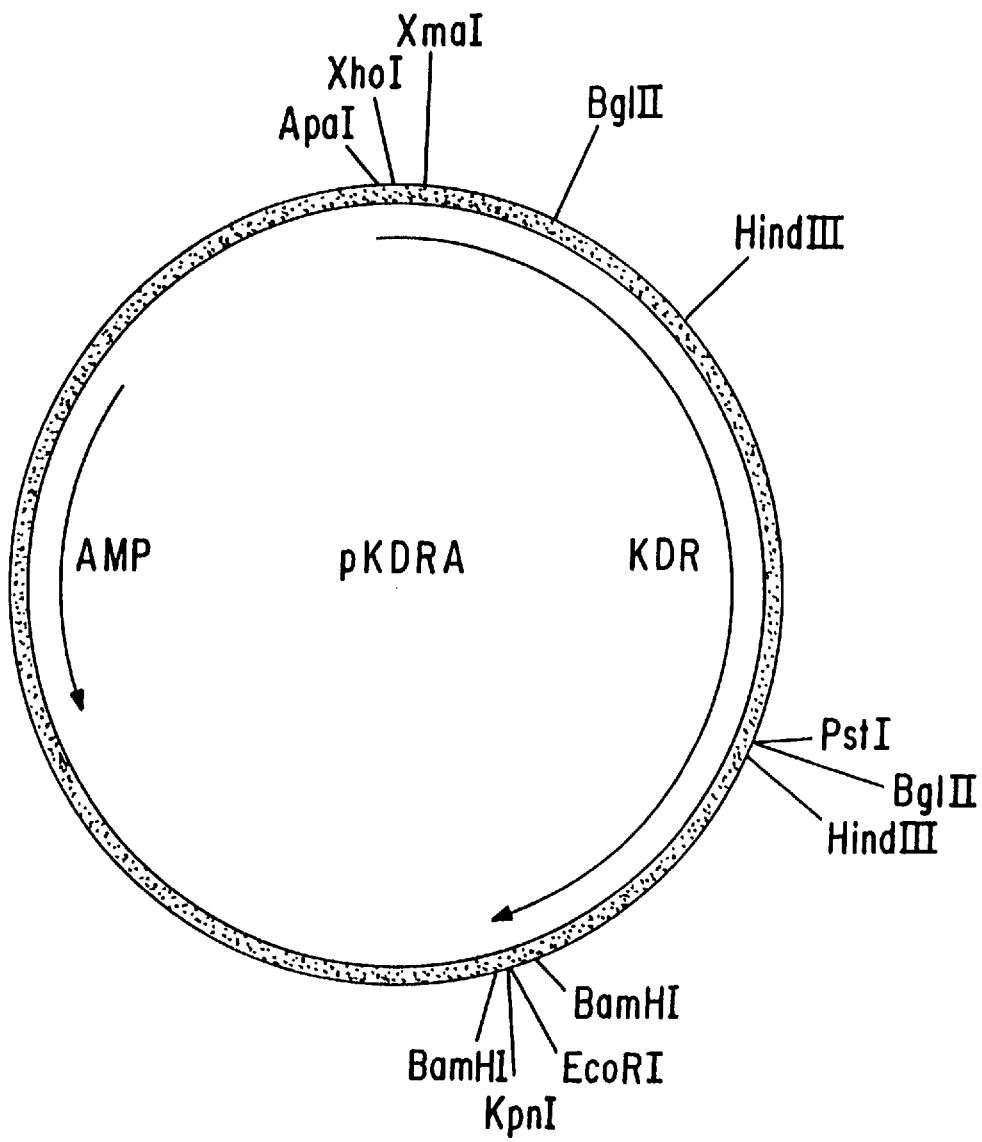
FIG. 17—A diagram of pKDRA is shown.

Soluble forms of KDR (a known VEGF receptor) [Terman, B. I. et al., (1991) Oncogene 6, pp. 1677–1683; Terman, B. I. et al., (1992) Biochem. Biophys. Res. Comm. 187, pp. 1579–1586] may exist naturally but have not yet been identified. A soluble form of KDR is recombinantly constructed by modifying its coding sequence by PCR using the primers 1) 5' TITTGGATCCCTGCAGACAGATC-TACGTfTGAGAACC 3' (SEQ. ID. NO.: 7) and 2) 5' TTTTGGATCCTTAACGCTCTAGGACTGTGAGC 3' (SEQ. ID. NO.: 8), and pKDRA (the Xhol/EcoRl fragment coding for the extracellular and transmembrane domain of KDR cloned into the EcoRI site of pGEM 7Z obtained from Promega) as a template (FIG. 17). This generated a translation stop codon after amino acid residue number 663 of KDR which corresponds to the extracellular domain of full length KDR. This modified fragment is then used to replace the Pstl/BamHl fragment of pKDRA generating a truncated form of the KDR gene (FIG. 10A–10B) which codes for a soluble receptor denoted sVEGF-RII (FIG. 11A–11B). The Xhol site at base pair number 257 is then changed to a BamHl site by standard cloning techniques. Another truncated form of the KDR receptor is created with primer 1 shown above, and primer 3) 5' GGATCCAACGGTC-CCTAGGATGATGAC 3', (SEQ. ID. NO.: 9) (FIG. 12A–12B). This form of KDR, denoted VEGF-RTMII, is truncated at the C-terminal side of the transmembrane domain and therefore retains the transmembrane region (FIG. 13). A similar form of the FLT receptor is generated by PCR using the primers 4) 5' AGCACCTTGGTTGTGGCT-GACTC 3' (SEQ. ID. NO.: 10) and 5) 5' TTTTGGATCCT-TAGATAAGGAGGGTTAATAGG 3' (SEQ. ID. NO.: 11) and plasmid pmFLT (full length fit cloned into the EcoRI site of pGEM3Z obtained from Promega) as a template (FIG. 16). The 780 base pair PCR fragment can then be cloned together with the EcoR1Xbal fragment from pmFLT to produce an EcoR1/BAMHl fragment (FIG. 14A–14B) encoding a truncated form of FLT (denoted VEGF-RTMI) which retains the transmembrane domain but lacks the cytoplasmic domain (FIG. 15). The EcoRl site at the 5' end of the gene is then modified to a BamHl site. The resulting truncated forms of KDR and FLT are then cloned into pBluebaclll (Stratagene) for expression in Sf9 insect cells. Characterization of these constructed truncated forms of VEGF receptors is accomplished by the techniques used to characterize sVEGF-RI as in Examples 2, 3, 4, 5, and 6.

EXAMPLE 8
Identification and Partial Purification of a Soluble VEGF Binding Protein A mRNA encoding a soluble version of Flt was expressed in HUVECs. The recombinant sFlt protein, when expressed in Sf9 insect cells (BVsFlt), was found to bind tightly to heparin Sepharose. To determine if sFlt protein was expressed by HUVECs, conditioned medium from cultured HUVECs was filtered through a 0.22 μm membrane and passed over a heparin sepharose column. The heparin column was eluted with a step gradient and fractions were tested for binding to [$^{125}$I] VEGF by covalent crosslinking. VEGF binding activity eluted at similar NaCl concentrations as the BVsFlt protein and was found in the 0.6–1.2M NaCl step fraction. An equal volume of EndoUV medium (endothelial cell growth medium) not conditioned was chromatographed and had no VEGF binding activity in the 0.6–1.2M NaCl fraction. The VEGF binding activity from HUVECs when crosslinked to labeled VEGF formed complexes which migrate slower on SDSIPAGE than VEGF complexes formed with BVsFlt. VEGF binding fractions were pooled and further separated by cation exchange chromatography with a linear NaCl gradient. Again, VEGF binding activity from the endothelial cell conditioned medium elutes at a similar position as BVsFlt.

The chromatography data shows that the partially purified HUVEC VEGF binding protein behaves similar to BVsFlt. To determine if this VEGF binding protein is related to Flt, antibodies against peptides based on the N-terminus and third immunoglobulin-like domain in the extracellular region of Flt were prepared. Fractions from the mono S column that produced high molecular weight complexes when covalently crosslinked to [$^{125}$] VEGF were analyzed by Western blot analysis. These data show that a 116 kDa protein band which co-elutes with VEGF binding activity was detected by both antibodies, thus the binding activity isolated from human endothelial cells is a soluble form of Flt.

---

What is claimed is:

1. A soluble VEGF inhibitor protein in substantially pure form which comprises the amino acid sequence as set forth in SEQ ID NO:6.

2. A composition comprising the inhibitor of claim 1 and a pharmaceutically acceptable carrier.

3. A soluble VEGF inhibitor protein in substantially pure form which consists of the amino acid sequence as set forth in SEQ ID NO:6.

4. A composition comprising the inhibitor of claim 3 and a pharmaceutically acceptable carrier.

* * * * *